US012627308B2

(12) United States Patent
Hashemi et al.

(10) Patent No.: US 12,627,308 B2
(45) Date of Patent: May 12, 2026

(54) STIMULATION AND RECORDING SYSTEM WITH MULTI-POINT ARTIFACT CANCELLATION

(71) Applicant: University Of Southern California, Los Angeles, CA (US)

(72) Inventors: Hossein Hashemi, Los Angeles, CA (US); Aria Samiei, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 679 days.

(21) Appl. No.: 17/986,432

(22) Filed: Nov. 14, 2022

(65) Prior Publication Data

US 2023/0198534 A1      Jun. 22, 2023

Related U.S. Application Data

(60) Provisional application No. 63/279,279, filed on Nov. 15, 2021.

(51) Int. Cl.
H03M 1/06       (2006.01)
A61N 1/36       (2006.01)

(52) U.S. Cl.
CPC ....... H03M 1/0617 (2013.01); A61N 1/36128 (2013.01)

(58) Field of Classification Search
CPC ......................... H01M 1/0617; A61N 1/36128
See application file for complete search history.

(56) References Cited

U.S. PATENT DOCUMENTS

| | | | | | |
|---|---|---|---|---|---|
| 3,745,257 | A | * | 7/1973 | Fudemoto | H04L 7/027 |
| | | | | | 375/242 |
| 6,148,229 | A | * | 11/2000 | Morris, Sr. | A61B 5/7207 |
| | | | | | 600/509 |
| 2006/0122529 | A1 | * | 6/2006 | Tsau | H03F 3/45 |
| | | | | | 600/544 |
| 2007/0150007 | A1 | * | 6/2007 | Anderson | A61N 1/05 |
| | | | | | 607/116 |
| 2009/0082691 | A1 | * | 3/2009 | Denison | A61B 5/374 |
| | | | | | 600/544 |
| 2016/0121109 | A1 | * | 5/2016 | Edgerton | A61N 1/36025 |
| | | | | | 607/45 |
| 2017/0273594 | A1 | * | 9/2017 | Liu | A61B 5/0531 |
| 2017/0338830 | A1 | * | 11/2017 | Price | H03M 1/1009 |

(Continued)

OTHER PUBLICATIONS

Adam E. Mendrela "A Bidirectional Neural Interface Circuit With Active Stimulation Artifact Cancellation and Cross-Channel Common-Mode Noise Suppression", IEEE Journal of solid-State Circuits, vol. 51, No. 4; pp. 955-965 (Year: 2016).*

(Continued)

*Primary Examiner* — Michael J Dalbo
*Assistant Examiner* — Kaleria Knox
(74) *Attorney, Agent, or Firm* — NIXON PEABODY LLP

(57) ABSTRACT

A system and method for reducing or eliminating undesired effects of an artifact on a received signal is disclosed. The signal is generated from stimulating a sample. A receiver includes estimations of artifacts on the signal that are subtracted at different stages of the receiver. The estimations of the artifact may be performed via a successive approximation register scheme.

21 Claims, 38 Drawing Sheets

(56) References Cited

U.S. PATENT DOCUMENTS

2018/0070925 A1* 3/2018 Chen .................. H03M 1/0617

OTHER PUBLICATIONS

Muhammad E. H. Chowdhury "Reference layer artefacts subtraction (RLAS): A novel method of minimizing EEG artefacts during simultaneous fMRI", Neuroimage, vol. 84, Jan. 1, 2014, pp. 307-319 (Year: 2014).*

Stanislay Culaclii "Online Artifact-Cancellation in Same electrode neural Stimulation and Recording Using a Combined Hardware and Software Architecture"; IEEE Trans Biomed Circuits Syst. Author manuscript; pp. 1-43 (Year: 2019).*

\* cited by examiner

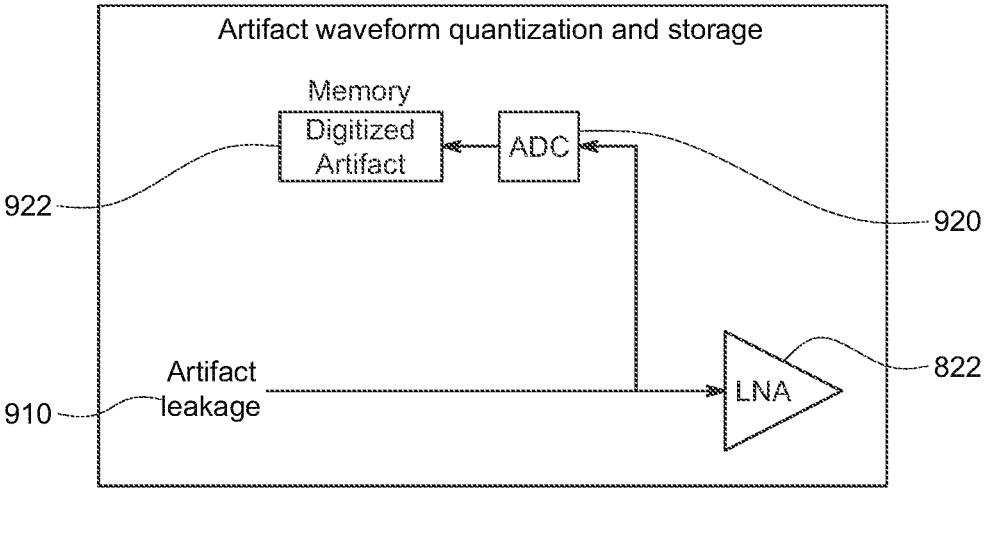
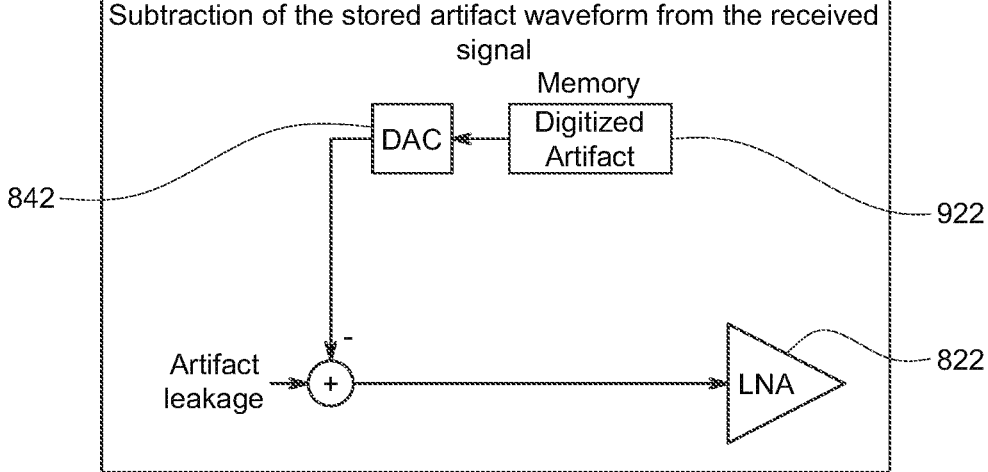
FIG. 9

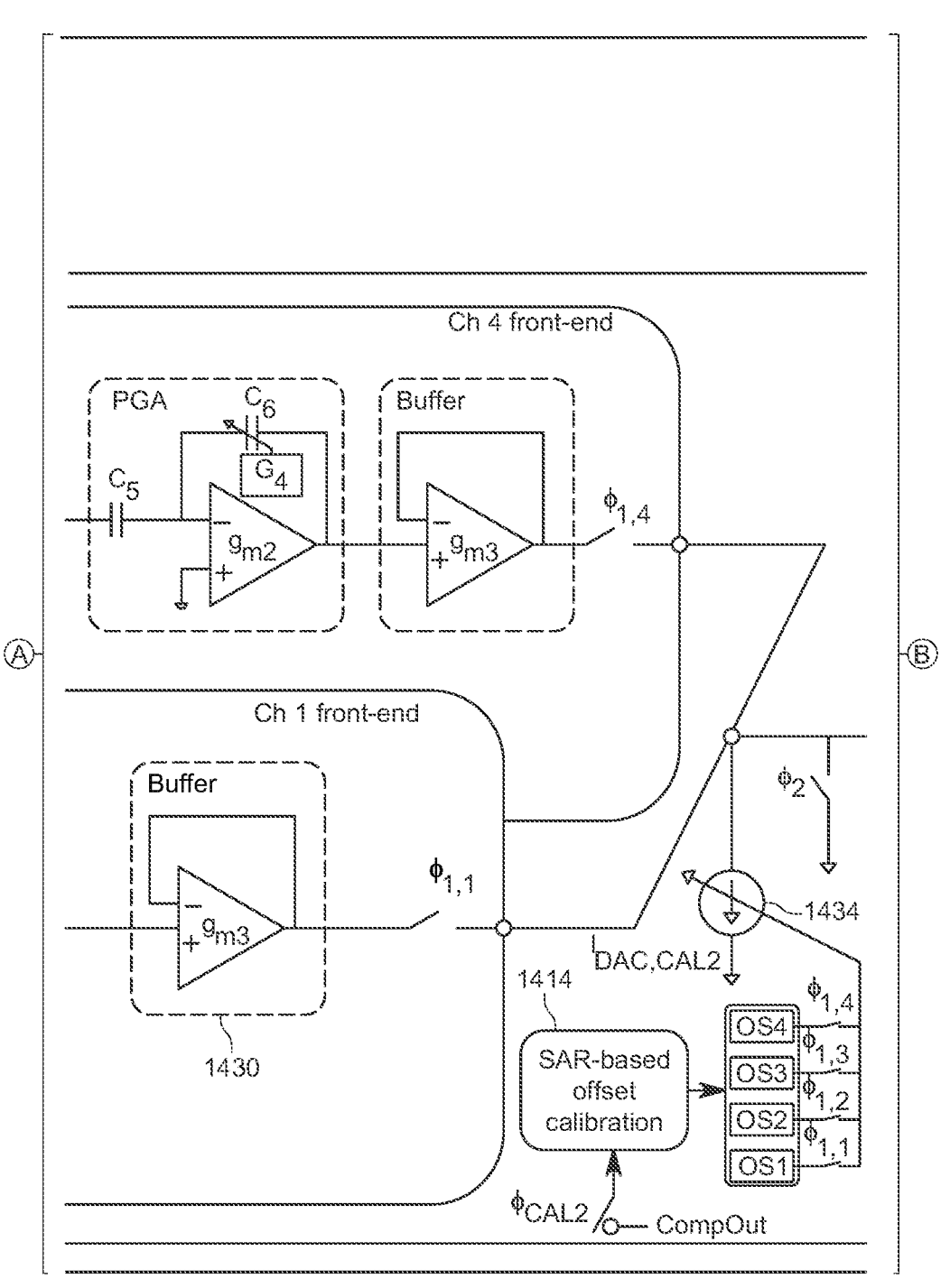
FIG. 14A (Continued...)

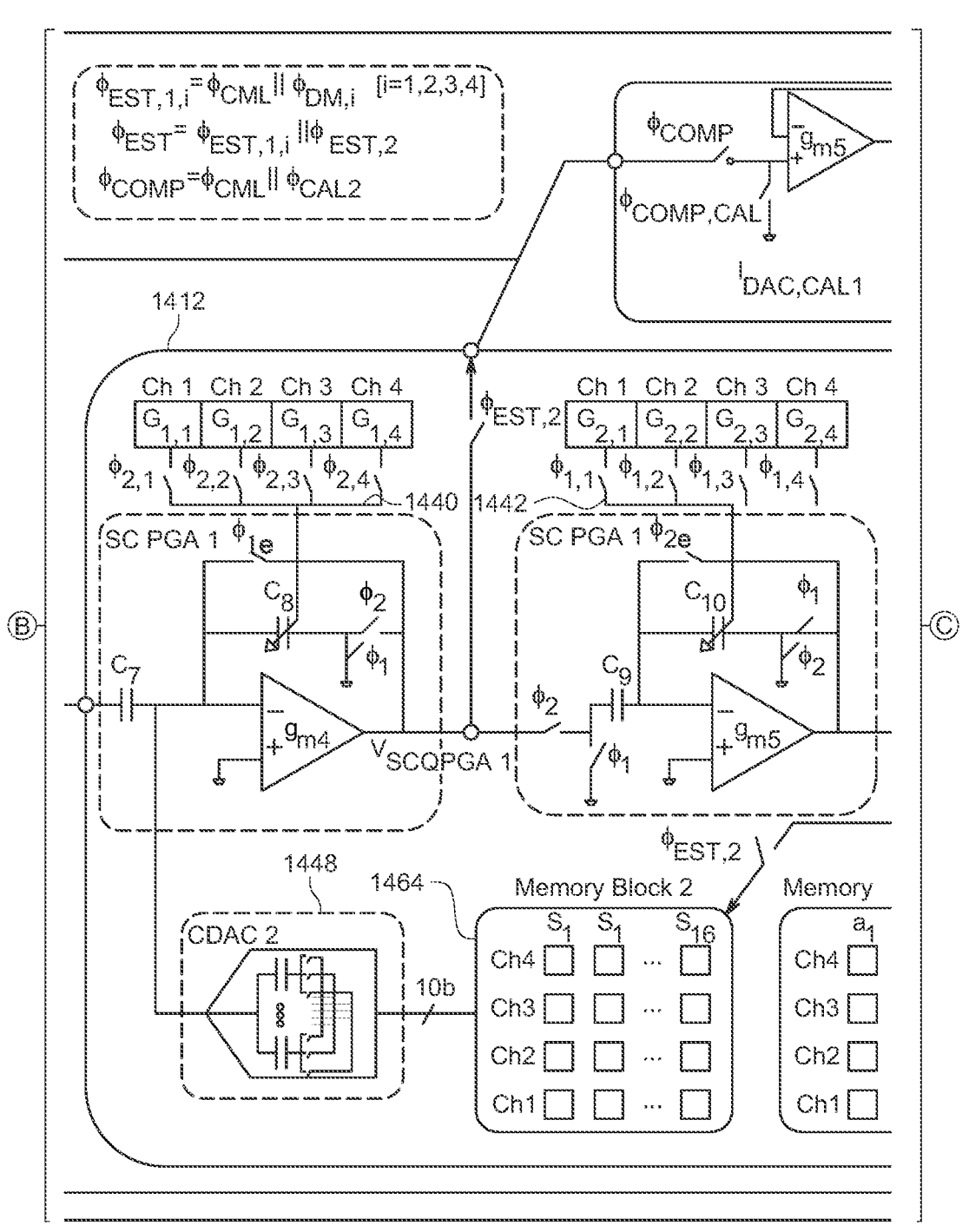
FIG. 14A (Continued...)

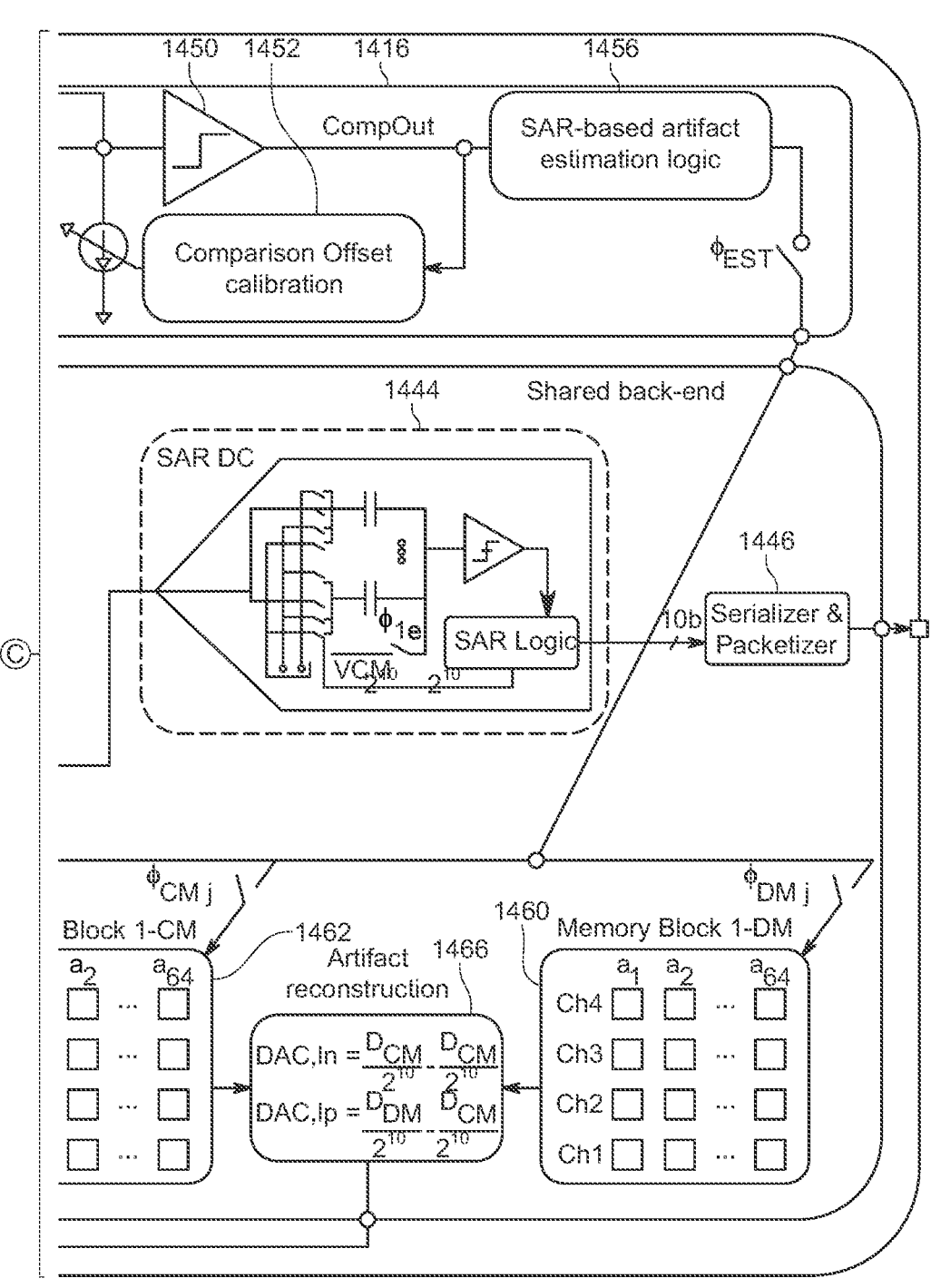
FIG. 14A (Continued...)

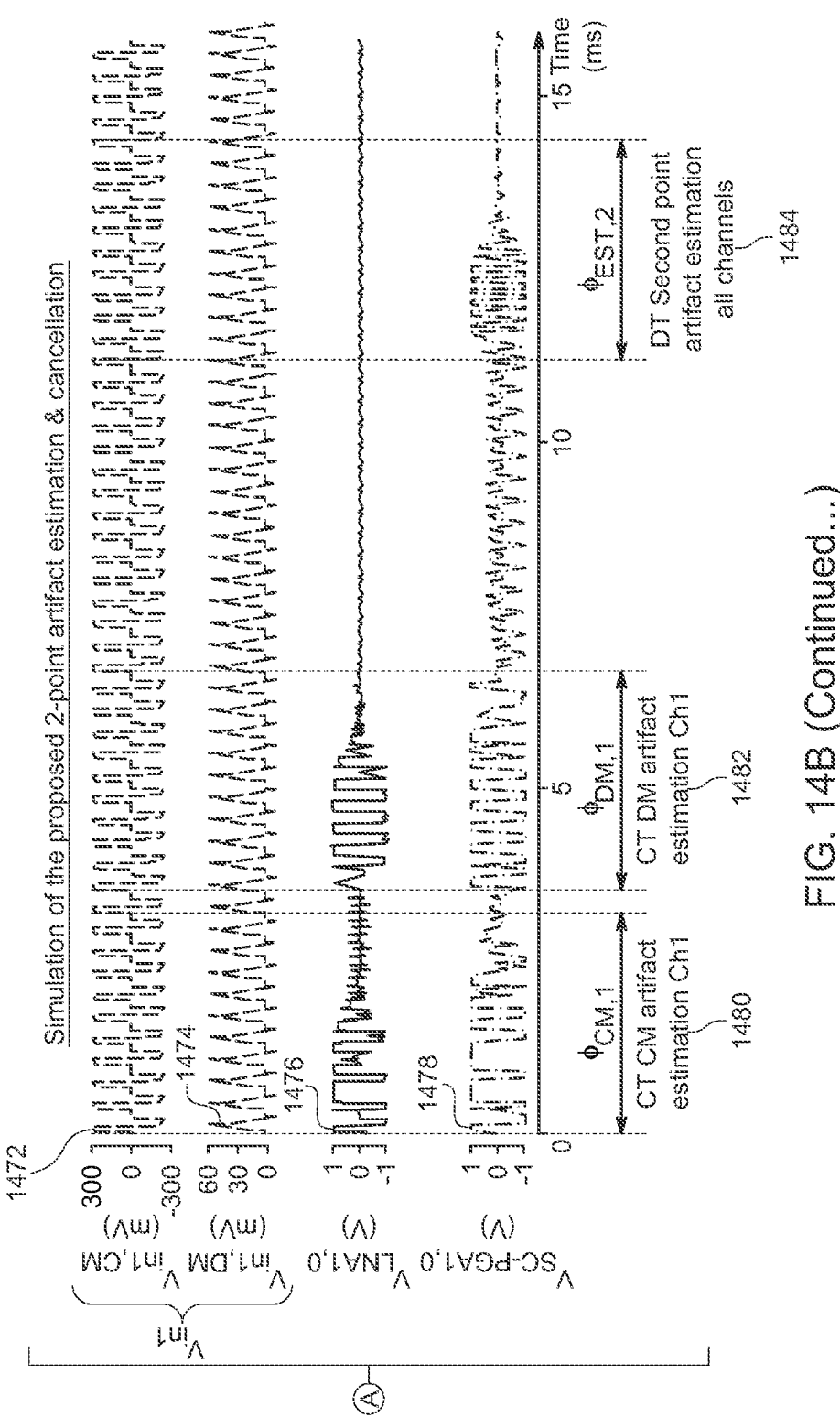
FIG. 14B (Continued...)

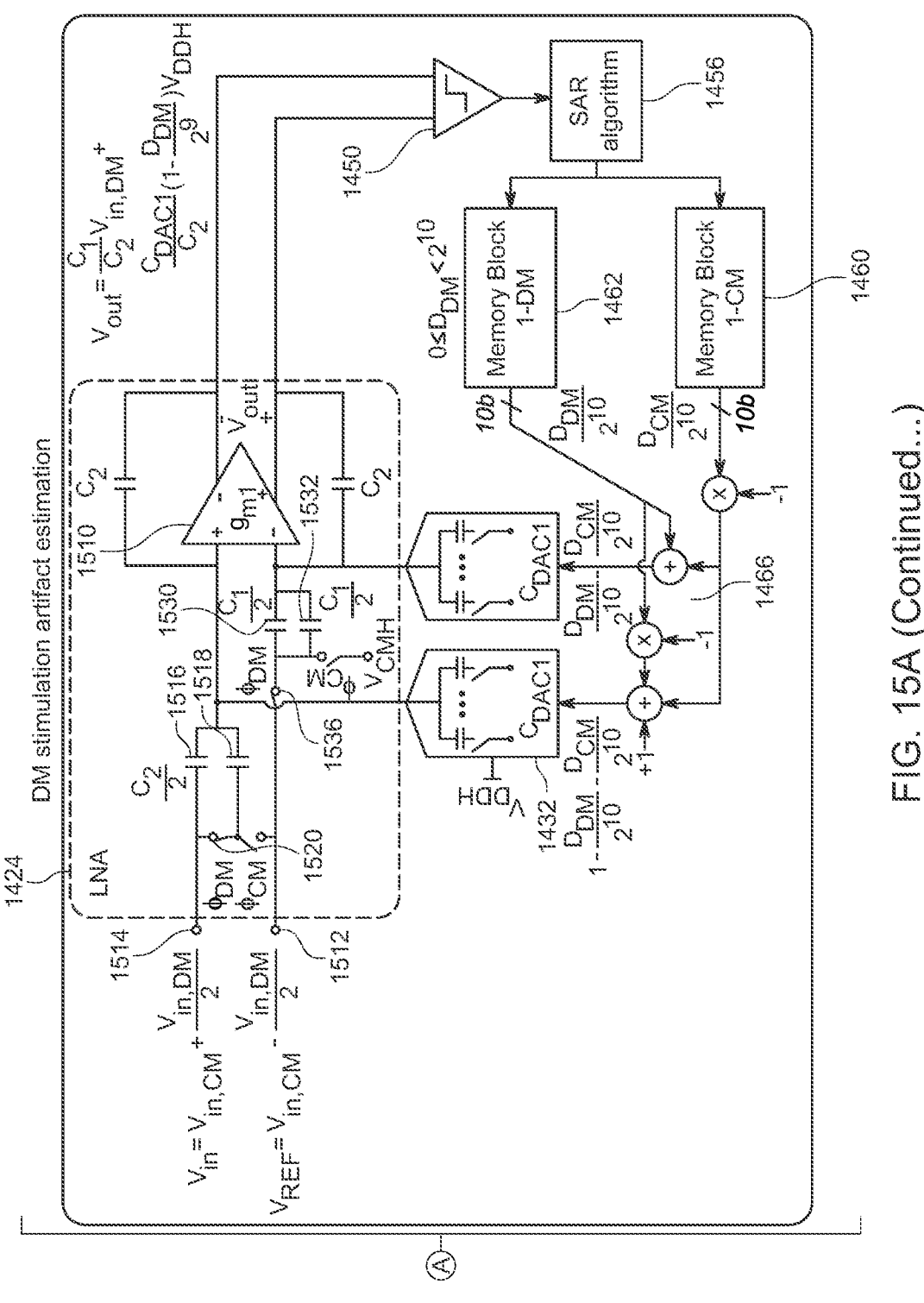
FIG. 15A (Continued...)

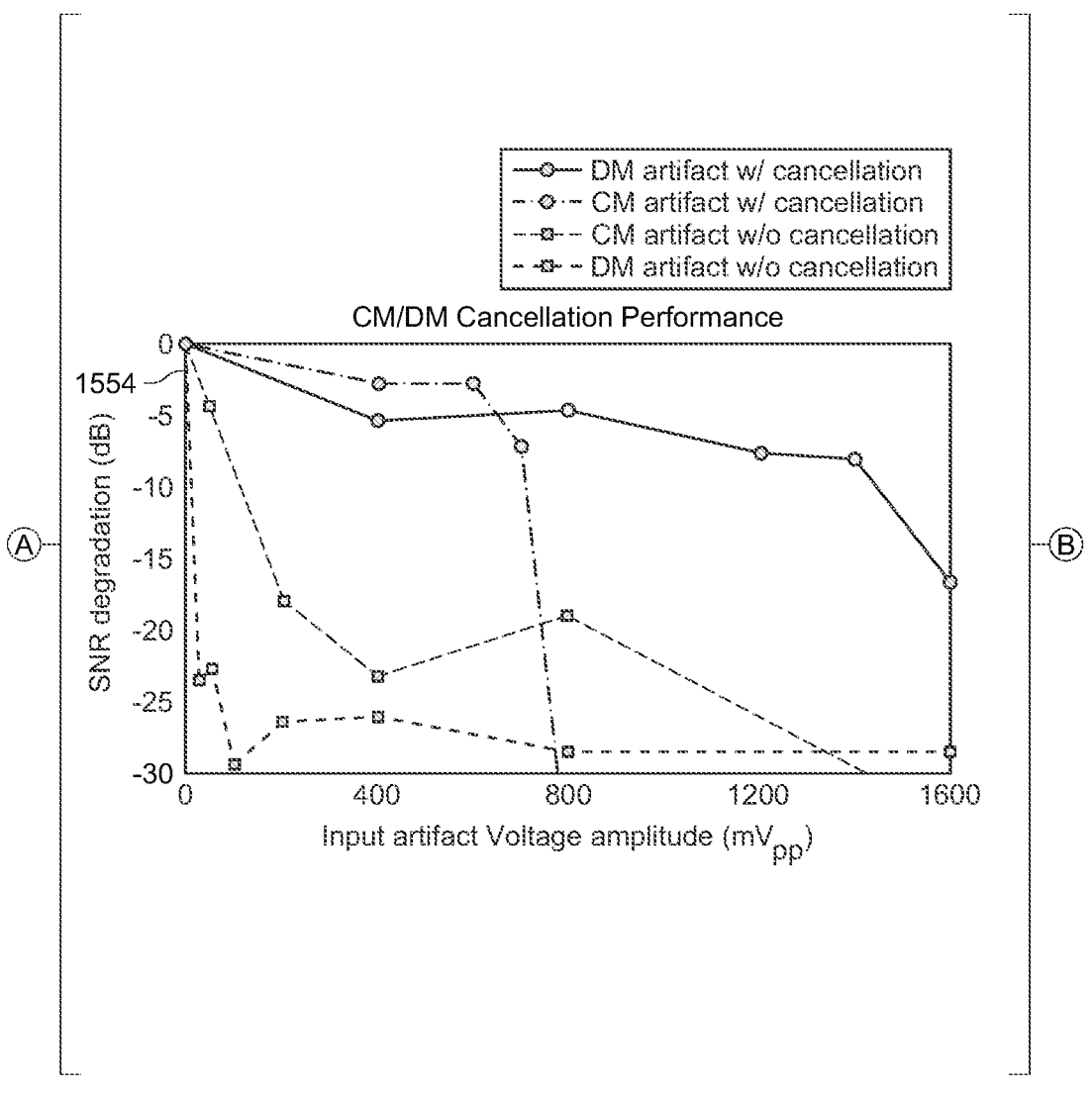
FIG. 15B (Continued...)

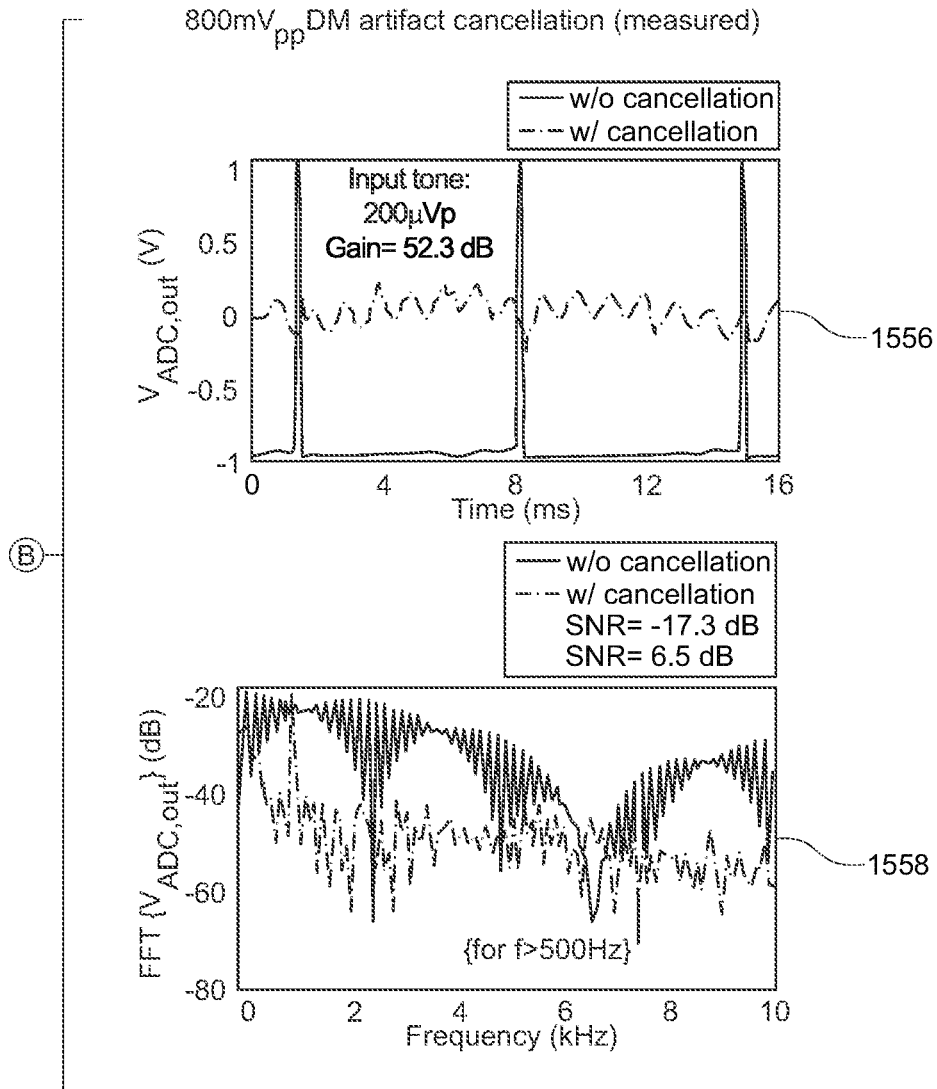
FIG. 15B (Continued...)

1670
Direct measurement of the SC-PGA2 differential output (at the ADC input)
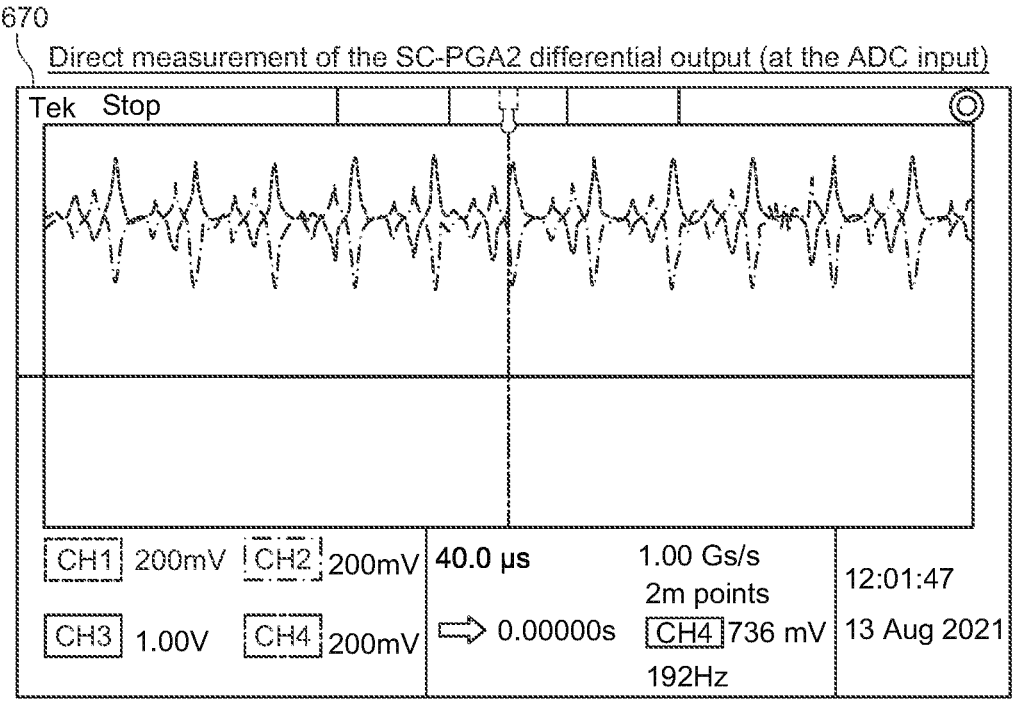
After automatic offset calibration
1672
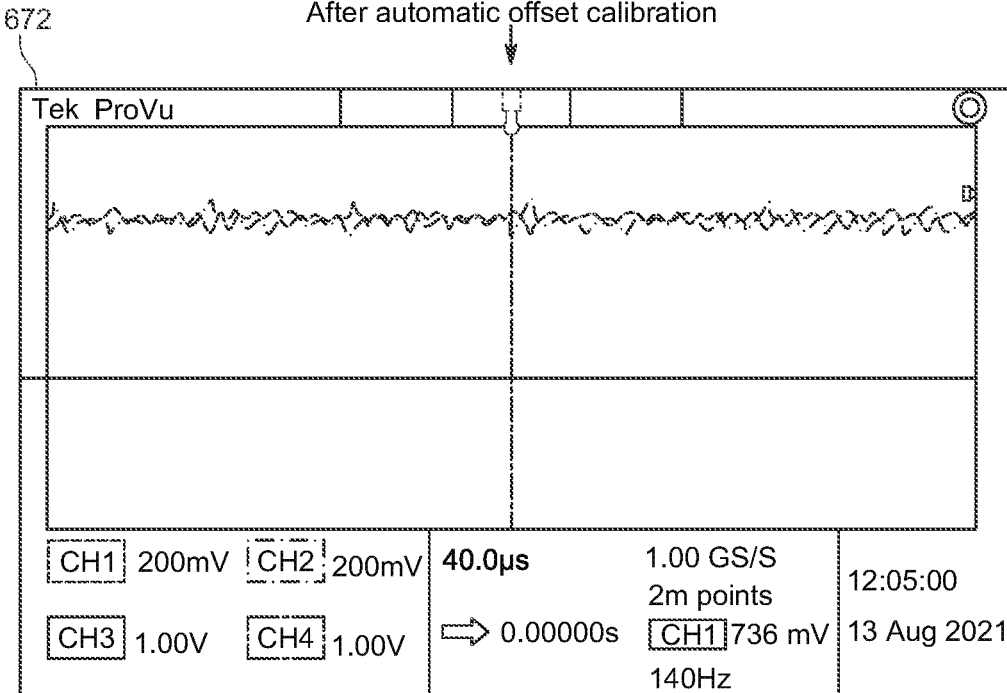
FIG. 16E SAR-based estimation algorithm and memory blocks Stimulation / Cancellation Control and Timing

CDAC2

SC-PGA

Oscillator & CLK Gen.

SAR-based Offset Cal.1

Comp.

SAR ADC

Ch-4  Ch-3  Ch-2  Ch-1

LNA  CDAC  STM

Biasing

1750

1732

1700

1742

1730

1740

1722

1734

1720

1718

1710

1712

1714

1716

1900

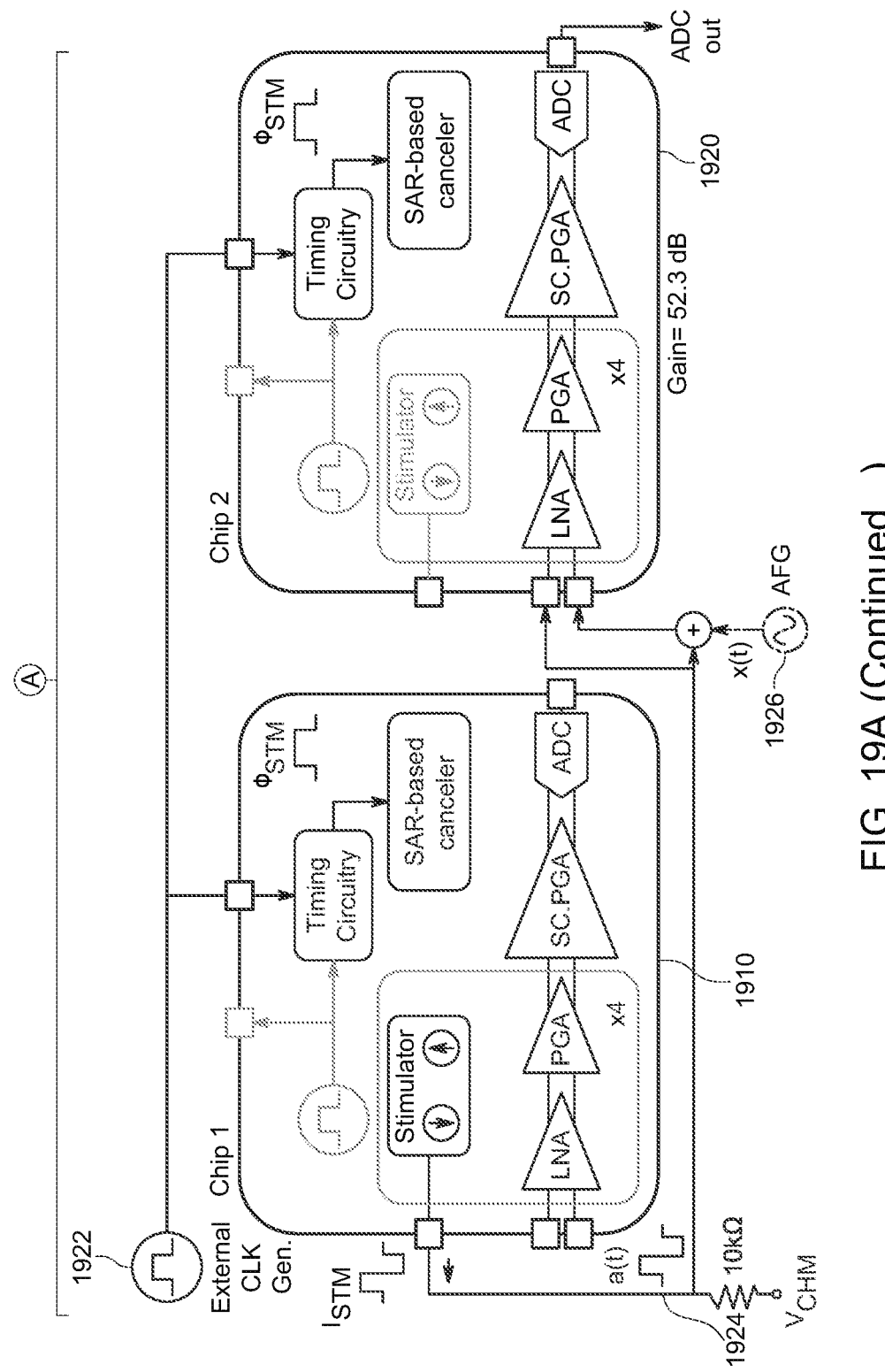
FIG. 19A (Continued...)

| | [1] ISSCC'21 | [2] JSSC'20 | [3] JSSC'18 | [4] ISSCC'20 | [5] JSSC'21 | This work |
|---|---|---|---|---|---|---|
| Technology (nm) | 65 | 130 | 40 | 180 | 180 | 180 |
| Supply voltage (V) | 1.2, 0.8 | 0.6,1.2,3.3 | 1.2 | 1.5 | 1, 3 | 1, 3 |
| Signal BW (Hz) | 1k | 1 - 500 | 1 - 5k | 0.1 - 1k | 200 - 9k | <10 - 9k |
| Voltage gain (dB) | NA | NA | 17.9 | 14 - 44 | 27.6 - 50.0 | 25.7 - 75.3 |
| In-ref. noise($\mu V_{rms}$) | 3.56 | 1.6 | 6.35 | 1.7 | 11 | 9.8 |
| ADC res. (bits) | 15 | 12 | 15 | 16 | 10 | 10 |
| Power/Ch($\mu$W) Rec.[a] | 10.05 | NA | 7.3 | 1.48 | 2.88 | 5.2 |
| Power/Ch($\mu$W) Canc.[b] | NA | 1.7 | NA | - | 1.42 | 2.7 |
| Rec. Area/Ch (mm$^2$) | 0.075 | 0.023 | 0.113 | 0.09 | 0.66 | 0.35 |
| # Rec/Stim. Channels | 1/0 | 32/32 | 1/0 | 8/2 | 8/2 | 4/4 |
| Stimulation artifact mitigation method | 2$^{nd}$-order VCO-based ΔΣ ADC | Δ$^2$Σ ADC | CTΔΣ ADC | FE adaptive FIR filter canceler | FE adaptive IIR filter canceler | 2-point CT-DT canceler |
| Max measured tolerable input stim. artifact (mVpp) DM | 60[c] | 200 | 200 | 500 | -500[d] | - 1200[d] |
| Max measured tolerable input stim. artifact (mVpp) CM | - | - | 700[d] | 1500 | -200[d] | - 700[d] |
| Max artifact suppression before quantization (dB) | NA | NA | NA | 35 | 37 | 68.5 (CM) / 58.1 (DM) |

NA: Not applicable. -: Not reported. a Recording blocks includes all the amplification stages, cancellation DACs and the ADC. b Cancellation logic and memory. c Motion artifact. d Defined as the artifact level that reduces the SNDR of the desired signal by 6dB (1-bit). e CCIA+ADC. f Noise integrated over the reported bandwidth.

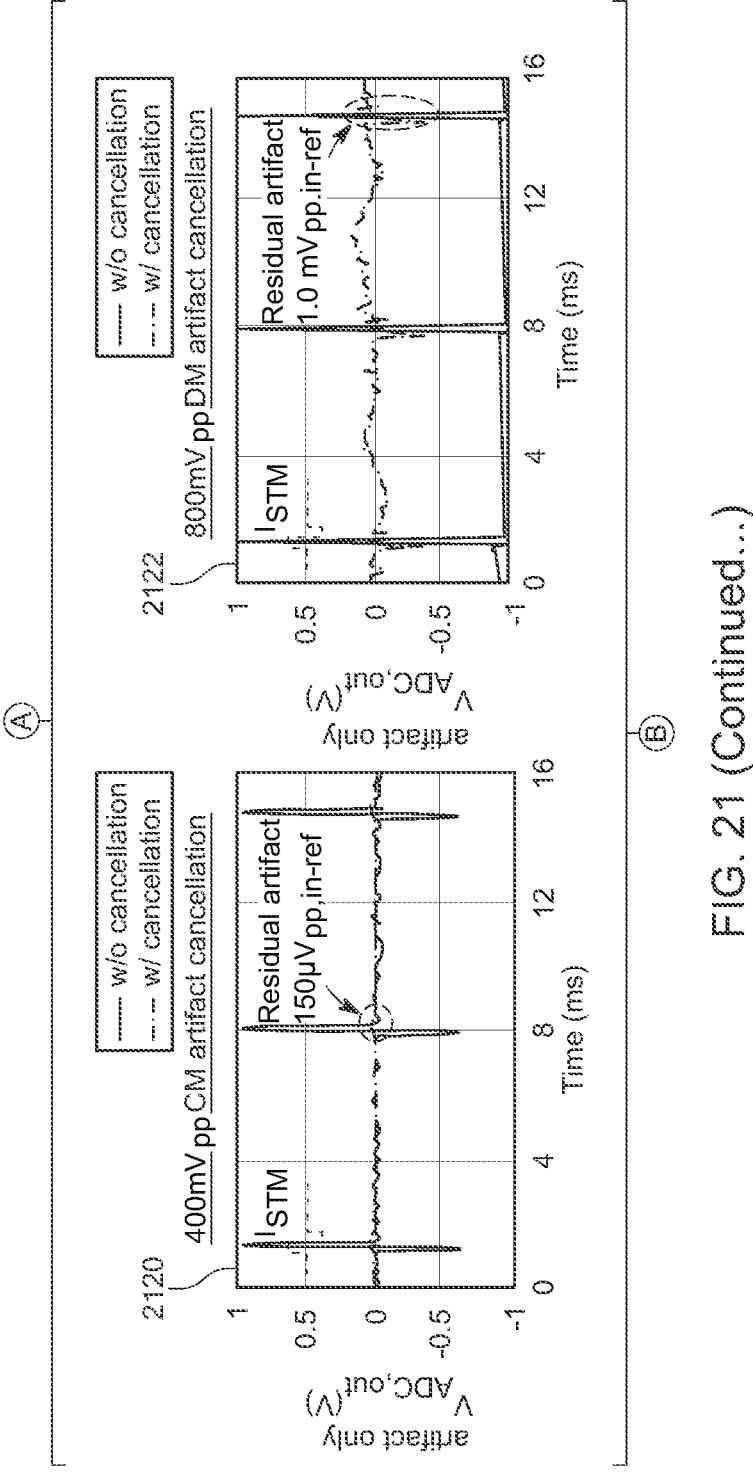
FIG. 21 (Continued...)

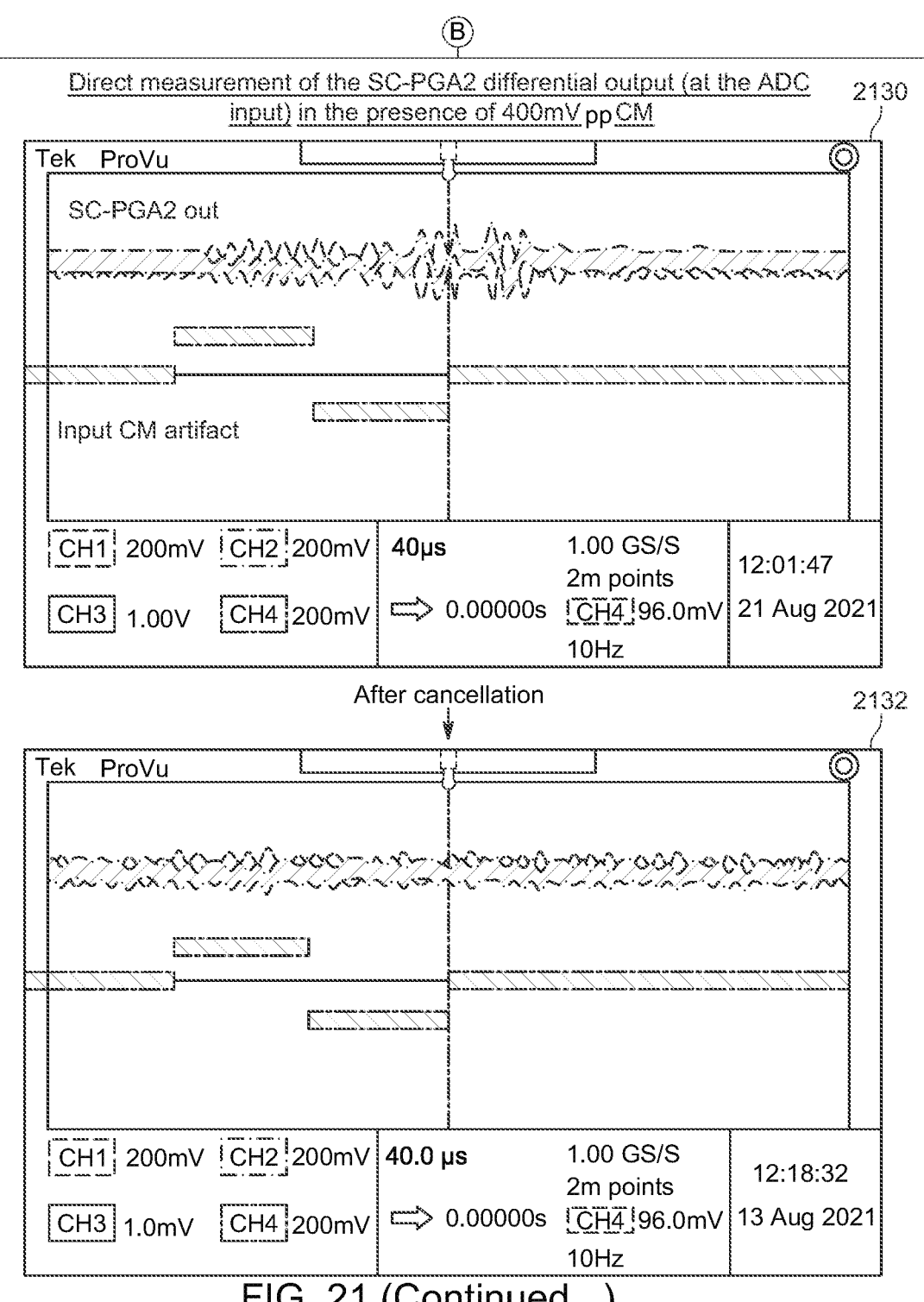
FIG. 21 (Continued...)

STIMULATION AND RECORDING SYSTEM WITH MULTI-POINT ARTIFACT CANCELLATION

PRIORITY CLAIM

This disclosure claims priority to and the benefit of U.S. Provisional Ser. No. 63/279,279 filed on Nov. 15, 2021. The contents of that application are hereby incorporated in their entirety.

STATEMENT REGARDING FEDERALLY SPONSORED RESEARCH OR DEVELOPMENT

This invention was made with government support under Grant Nos. NS099703 awarded by National Institutes of Health and CBET1343193 awarded by the National Science Foundation. The government has certain rights in the invention.

FIELD

The present disclosure relates to systems that include signal generation and signal recording functions. Specifically, certain aspects of the disclosure relate to biomedical systems that include electrical, magnetic, optical and acoustic stimulation and recording functions.

BACKGROUND

Currently, responsive neurostimulation (RNS) systems are being surgically implanted in patients with epilepsy. These devices continuously monitor the electrocorticography (ECoG) signals and look for patterns that can lead to seizures. Once the pattern is detected, stimulation signals are delivered to depth electrodes to prevent seizures. However, such devices lack the capability of simultaneous stimulation and recording of neural signals.

Closed-loop brain-machine interfaces have become critical components in neuroscience research and clinical applications such as the RNS systems for epilepsy. These systems record the neural activity, perform signal processing algorithms, and generate a specific spatiotemporal pattern to stimulate the neurons in the brain. Unfortunately, stimulation of the brain tissue introduces an artifact at the recording channels, which can significantly degrade the received signal quality.

One approach to overcome the artifact issue is to use oversampling analog to digital converters (ADCs) to increase the linear dynamic range (DR) of the front-end (FE) and accommodate the large artifacts on top of the neural signals. However, increasing the ADC resolution from a conventional 10 bits to ~15 bits (equivalent to 30 dB boost in dynamic range) drastically increases the energy required for the raw data transmission or on-chip back-end digital processing for artifact removal. An alternative approach is to estimate and cancel the artifact at the front end using adaptive digital filters, which can potentially relax the dynamic response requirements of the ADC. However, the existing front end cancellation techniques provide a limited artifact suppression (<40 dB) which reduces a 1000 mVpp artifact to about 10 mVpp swing. This residual artifact is about 1-2 orders of magnitude larger than the action potentials and the local field potentials (50-500 µVpp), which limits the effective number of bits (ENOB) allocated to the quantization of the target neural signals.

In many systems, it is advantageous or necessary to allow for simultaneous stimulation and recording of electrical signals. For instance, some biomedical systems should record physiological or neural signals while simultaneously providing appropriate stimulation signals to the tissues or neurons. In these systems, influences on the stimulation signal can directly or indirectly corrupt the recordings. Such influences are references such as signal artifacts that may be a result of external or internal sources. Existing methods that facilitate simultaneous recording and stimulation are bulky, consume significant power, require technologies that support high voltages, and often are unable to completely or meaningfully remove the undesired effects of stimulation signals from the recordings.

Further limitations and disadvantages of conventional and traditional approaches will become apparent to one of skill in the art, through comparison of such systems with the present disclosure as set forth in the remainder of the present application with reference to the drawings.

SUMMARY

One disclosed example is a signal recorder for a stimulation system that has an input receiving an input signal from a sample stimulated by a stimulation signal. The input signal includes an artifact. A first artifact estimation logic is coupled to the input producing a first artifact estimate. A first subtraction logic subtracts the first artifact estimation from the input signal. A second artifact estimation logic is coupled to the input signal producing a second residual artifact estimate. A second subtraction logic subtracts the estimate of the residual stimulation artifact from the input signal. An analog to digital converter (ADC) receives the input signal after subtraction of the estimates of the artifact and outputs an output signal.

Another disclosed example is a method of canceling an artifact on an input signal generated from a sample by a stimulation signal. The input signal is measured from the sample. A first estimation of the artifact is determined. A second artifact estimation of a residual of the artifact on the input signal is determined. The first artifact estimation is subtracted from the input signal input to a low noise amplifier. The second artifact estimation is subtracted from the input signal input to a gain amplifier.

Disclosed is a system and/or method for reducing or eliminating the undesired effects of generated signal on the received signal in a system that is capable of concurrent generation (or stimulation) and reception (or recording) of signals substantially, as shown in and/or described in connection with at least one of the figures, as set forth more completely in the claims.

Various advantages, aspects and novel features of the present disclosure, as well as details of an illustrated embodiment thereof, will be more fully understood from the following description and drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 9 illustrates a diagram of direct quantization and storage of the artifact to cancel the artifact during recording according to one or more embodiments of the present disclosure.

FIG. 16E shows graphs of the measured functionality of the offset calibration scheme in FIG. 16D according to one or more embodiments of the present disclosure.

FIG. 20 is a table illustrating a performance summary and comparison with the state-of-the-art neural interfaces resilient to artifacts.

DETAILED DESCRIPTION

Figure 1:
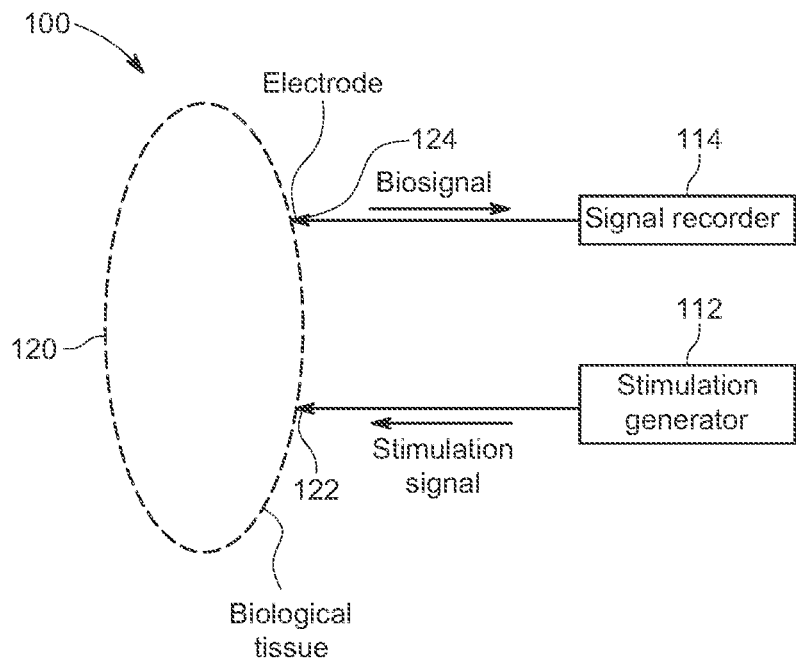
FIG. 1 illustrates a block diagram of a prior art stimulation system that includes a signal recorder and a stimulating signal generator.

As utilized herein the terms "circuit" and "circuitry" refer to physical electronic components (i.e., hardware) and any software and/or firmware ("code") which may configure the hardware, be executed by the hardware, and/or otherwise be associated with the hardware. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g." and "for example" set off lists of one or more non-limiting examples, instances, or illustrations.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

Illustrative embodiments are now described. Other embodiments may be used in addition or instead. Details that may be apparent to a person of ordinary skill in the art may have been omitted. Some embodiments may be practiced with additional components or steps and/or without all of the components or steps that are described.

Many systems are capable of generating and receiving signals. In some systems, it is desirable or essential for signal generation and reception to occur simultaneously. For instance, in some biomedical applications, it is necessary or desirable to monitor or record the physiological or neural signals while generating stimulating signals and applying them to tissues of neurons. In some of these systems, it is desirable to continuously monitor the physiological or neural signals as the stimulating signals are generated or applied. In such systems, the generated or applied signals may directly or indirectly corrupt or interfere with the monitored or recorded signals.

For instance, in some systems physiological neural activities are monitored or recorded to identify anomalies, infer intention, etc. At the same time, depending on the monitored or recorded signals, appropriate signals are generated and applied to the tissues or neurons. Alternatively, stimulating signals might be applied while the physiological or neural activities are monitored to understand the effect of stimulations.

In the remainder of this application, unless otherwise stated, the terms "recording", "receiving", and "monitoring" are used interchangeably. For instance, "recording physiological or neural activities", "receiving physiological or neural activities", and "monitoring physiological or neural activities" imply the same.

In the remainder of this application, unless otherwise stated, there is no distinction between "generating signals", "stimulating signals", and "applied signals" in the context of their adverse effect on the recorded signals, and the related mitigation strategies. For instance, "cancelling the stimulation artifact on the recorded signal", "cancelling the stimulating signal artifact on the monitored signal", "cancelling the undesired leakage of generated signal on the received signal", "cancelling the undesired feedback of the applied signal to the received signal" imply the same.

In the remainder of this application, unless otherwise stated, "artifact" refers to any undesirable signal that leaks into the recording system and is generated by the stimulation circuitry, which can be one or more of electrical stimulation, magnetic stimulation, optical stimulation and acoustic stimulation.

In the remainder of this application, unless otherwise stated, "biosignal", "biosignal", "biological signal", and "physiological signal" refer to any desirable signal that the recording system records.

In the remainder of this application, unless otherwise stated, "biological tissue" refers to any living tissue that can be in the form of an individual cell, or a population of cells. It can also refer to different organs in an animal or a human (e.g. brain, spinal cord, etc.) or the body as a whole (e.g. human body).

To overcome the limited artifact suppression of the existing solutions, the example system employs a two-point artifact suppression technique that cancels the stimulation artifact in two points along the signal amplification stages. This technique boosts the common-mode and differential-mode stimulation artifact suppression to 68.5 dB and 58.1 dB, respectively, which is an order of magnitude higher than the current state-of-the-art cancellation techniques.

FIG. 1 shows a known stimulation and recorder system 100 that includes a stimulation generator 112 and a signal recorder 114. The stimulation and recorder system 100 stimulates a target area 120, which may be tissue. The stimulation generator 112 includes an electrode 122 that applies an electrical signal to the tissue 120. An electrode 124 is attached to the signal recorder 114 to detect signals from the tissue 120.

The signal recorder 114 may monitor the signals at the same or a different location that the stimulating signal from the stimulation generator 112 is applied to. Instead of the two electrodes 122 and 124, a single electrode that applies the stimulating signal and conducts a detected signal to the signal recorder 114 may be used.

Figure 2:
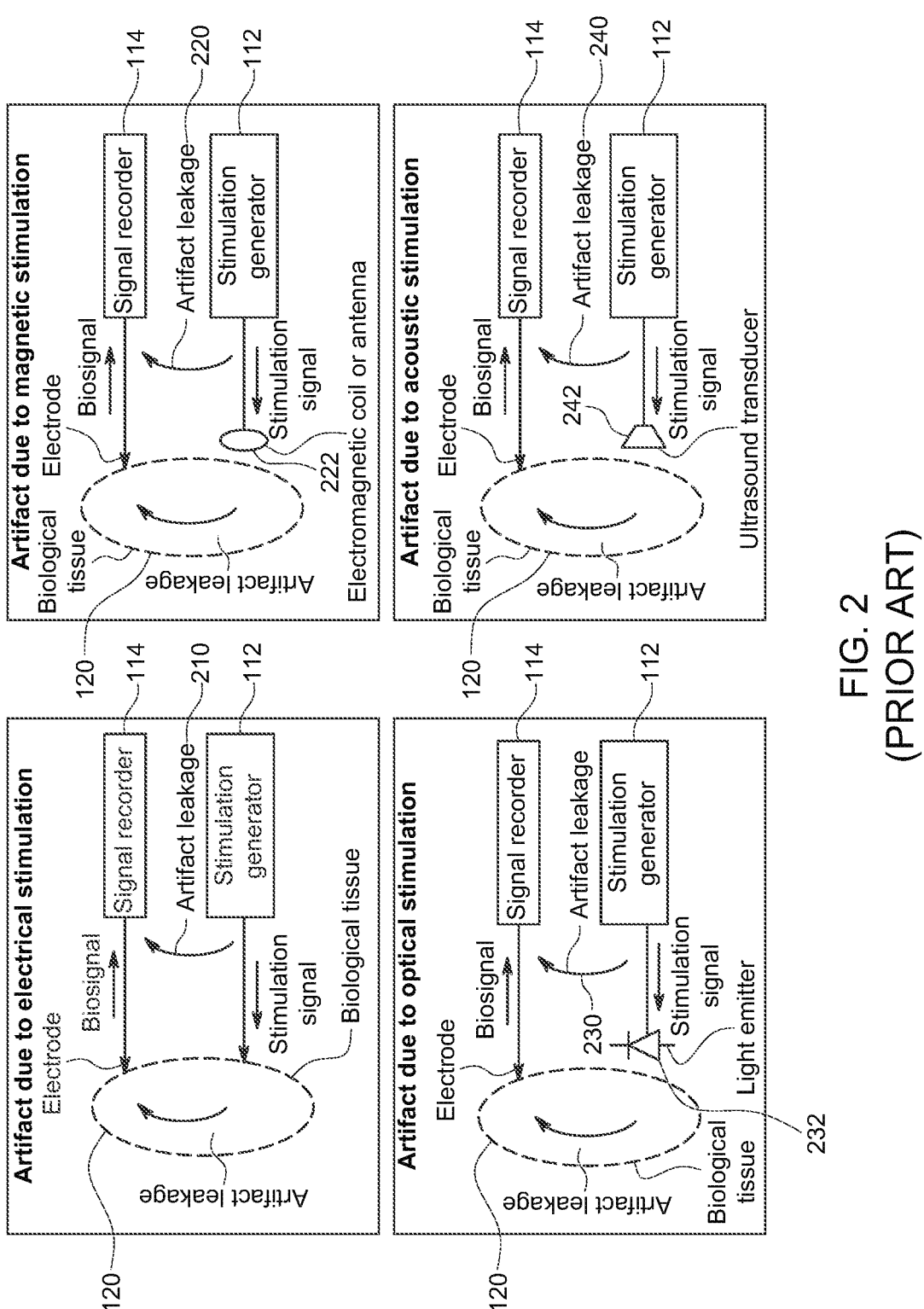
FIG. 2 illustrates a block diagram of a prior art stimulation system that show different sources of undesirable artifacts that may distort the signal recorded.

FIG. 2 shows a number of situations where artifact leakage may occur in the stimulation and recording system 100 in FIG. 1. Like elements in FIG. 2 are labeled with identical reference numbers as their counterparts in FIG. 1. A first example in FIG. 2 is electrical stimulation creating artifact leakage 210 from the stimulation generator 112. A second example in FIG. 2 is artifact leakage 220 occurring due to magnetic stimulation such as from an electromagnetic antenna 222. A third example in FIG. 2 is artifact leakage 230 occurring due to optical stimulation such as from a light emitter 232. A fourth example in FIG. 2 is artifact leakage 240 occurring due to acoustic stimulation such as from an ultrasound transducer 242.

In the examples of artifact leakage in FIG. 2, the artifact leakage might be intrinsic or extrinsic to the stimulation and recording system 100. For instance, the mere proximity of the recording and stimulating sites can cause an unwanted leakage. This leakage may happen due to electro-magnetic, opto-electronic, and piezoelectric effects depending on the modality of stimulation (magnetic, optical, and acoustic, respectively).

Figure 3:
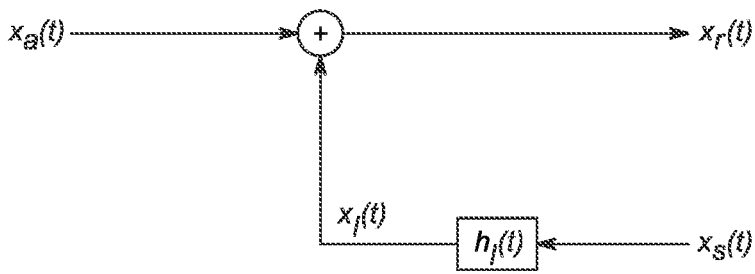
FIG. 3 illustrates a mathematical model of the system in FIG. 2 showing the artifacts.

Referring to FIG. 3, the leakage path between the stimulating signal generator and the signal recorder is modelled with a linear impulse response $h_l(t)$. $H_l(s)$ represents the Laplace transform of $h_l(t)$ which is commonly referred to as the transfer function. While a linear time invariant system is shown, the systems and methods discussed henceforth are also applicable to time variant systems as well. $h_l(t)$ is typically not known apriori, and in fact, may depend on the environment in which the system is deployed, and may vary over time. Therefore, the signal recorder 114 in FIGS. 1-2 will receive a combination of the intended signal $x_a(t)$ and the unwanted leakage signal $x_l(t)=x_s(t)*h_l(t)$, where $x_s(t)$ is the stimulating signal and * represents convolution. In other words, the recorded signal is given by $x_r(t)=x_a(t)+x_s(t)*h_l(t)$.

Ideally, the signal recorder 114 in FIG. 1 should only record $x_a(t)$. Unfortunately, the leakage term $x_s(t)*h_l(t)$ corrupts such an ideal recording. The leakage term may be from an intrinsic or extrinsic source to the system as shown in FIG. 2. If $h_l(t)$ can be extracted or estimated, and since $x_s(t)$ is known, the undesired leakage may be cancelled.

Figure 4:
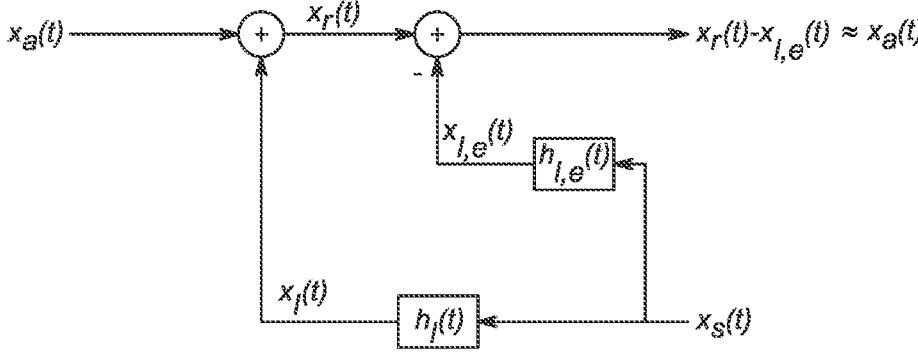
FIG. 4 illustrates a mathematical model of a system in a near replica of the undesired leakage signal that is generated and subtracted from the contaminated signal.

FIG. 4 shows a system and a corresponding mathematical model in which the leakage impulse response is estimated as $h_{l,e}(t)$ and is used to create a near replica of the undesired leakage signal $x_l(t)$ as $x_{l,e}(t)=x_s(t)*h_{l,e}(t)$. The signal recorder can now record $x_r(t)-x_{l,e}(t)=x_a(t)+x_s(t)*(h_l(t)-h_{l,e}(t))$ which will be equal or close to $x_a(t)$ if $h_{l,e}(t)\simeq h_l(t)$.

Figures 5, 6:
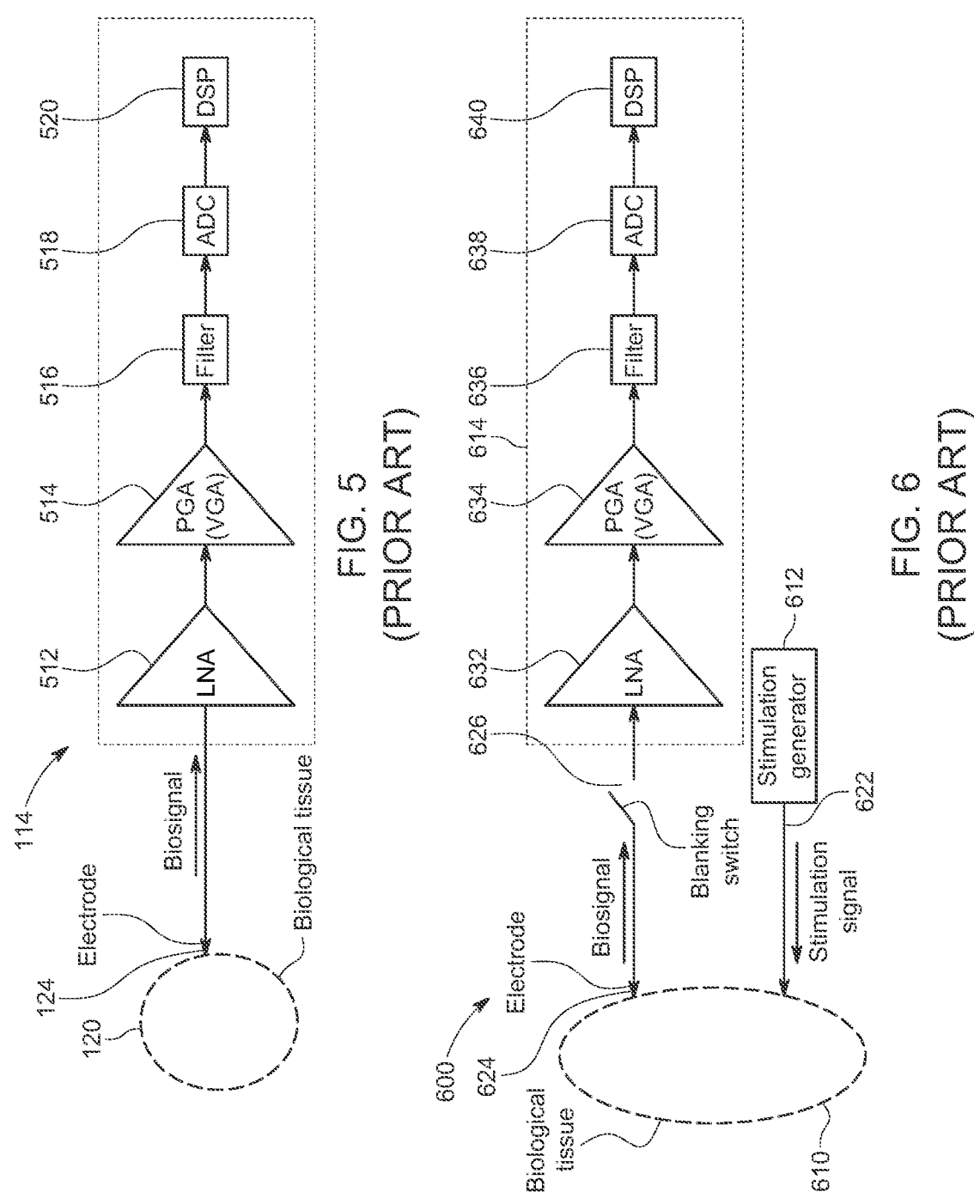
FIG. 5 illustrates a functional architecture of a typical prior art signal recorder.
FIG. 6 illustrates a functional architecture of a prior art stimulation signal generator and a signal recorder with an artifact blanking switch.

FIG. 5 shows a more detailed functional architecture of the typical known signal recorder 114 in FIG. 1. The example signal recorder 114 includes the electrode 124. Signals from the electrode are fed to a low-noise amplifier (LNA) 512, a variable gain amplifier (VGA) 514 also known as a programmable gain amplifier (PGA), a filter 516, an analog to digital converter (ADC) 518, and a digital signal processor (DSP) 520. It is possible that the functions of some or all of these blocks are incorporated in a single functional block. For example, a variable gain amplifier with filtering function can be realized. As another example, the low noise amplifier 512 may be designed to incorporate variable gain.

The electrode 510 serves as the interface between the physical world and the signal recorder 500. In other words, the electrode 510, if needed, converts the desired quantities (e.g., physiological or neural activities) to electrical signals, and then transfers the electrical signals to the electronic part of the signal recorder 114. The LNA 512 boosts the typically small level of desired signals that are picked up by the electrode 510 without adding significant noise. The VGA/ PGA 514 adjusts the level of signals to an appropriate level for the ADC 518. For instance, smaller signals may require more amplification whereas larger signals may require less amplification. The filter 516 removes the unnecessary signals and noise from the desired signal. The ADC 518 converts the analog signals to digital signals for further processing in the DSP 520.

Many electronic circuits, including amplifiers, active filters, and analog to digital converters use a voltage supply to operate. The maximum level of signals that these blocks can handle without distorting the signals is limited by the supply voltage, power consumption, as well as the specific implementation of each block. Therefore, linear active blocks capable of handling large signals often need to use high supply voltages and/or consume large power. On the other hand, in many applications, it is desirable or essential that the circuits operate from low voltages and consume little power. Other considerations including noise, footprint, and bandwidth also affect the design of electronic circuits.

In some applications, the signal that is coupled or leaked from the stimulating signal generator to the signal recorder is significantly larger than the desired signal to be recorded. In presence of such large undesired leakage signals, the recorder circuitry will either need to use large supply voltages and/or consume large power; otherwise the large undesired leakage causes unwanted signal distortion for the desired signal to be recorded.

FIG. 6 shows the block diagram of a prior art recording and stimulation system 600 that includes a stimulating signal generator 612 and a signal recorder 614. The stimulating signal generator applies a stimulation signal to a tissue sample 610 via an electrode 622. An electrode 624 transmits the generated signal from the tissue sample 610 to the signal recorder 614. The signal recorder input is disconnected from the electrode 624 during the times of stimulation through a blanking switch 626 so as to block a significant portion of the unwanted leakage to the signal recorder 614. In this example, the signal recorder 614 includes low-noise amplifier (LNA) 632, a variable gain amplifier (VGA) 634, a filter 636, an analog to digital converter (ADC) 638, and a digital signal processor (DSP) 640. The signal recorder 614 in the prior art system 600, however, cannot record signals at the times of stimulation, i.e., no concurrent stimulation and recording is supported due to the blanking switch 626 being open to block the unwanted leakage.

Figure 7:
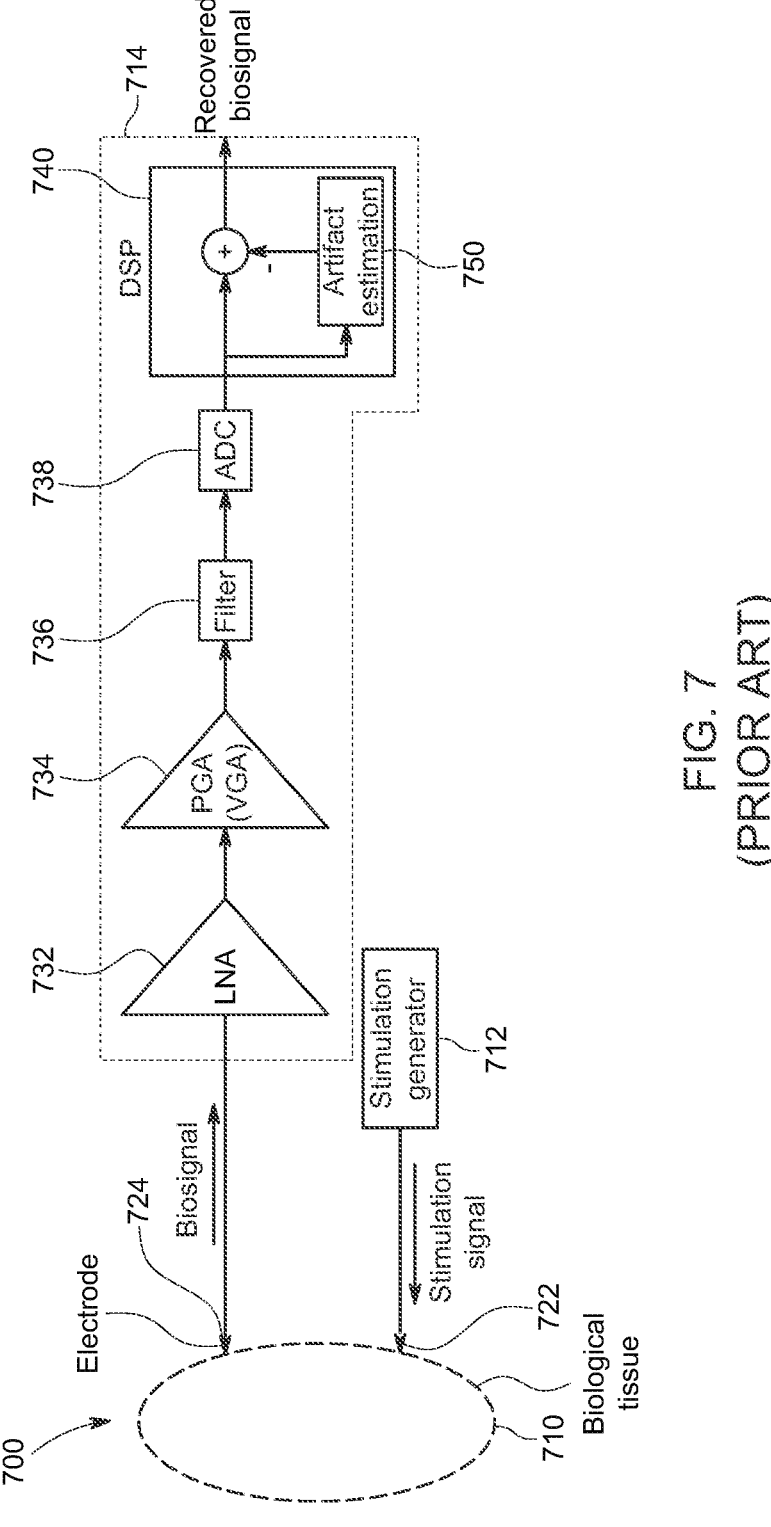
FIG. 7 illustrates a functional architecture of a prior art stimulation signal generator and a signal recorder with single artifact estimation and cancellation in a digital signal processor (DSP).

FIG. 7 shows the block diagram of a known system 700 that uses a single estimate of the artifact to cancel the unwanted leakage. The system 700 includes a stimulating signal generator 712 and a signal recorder 714. The stimulating signal generator applies a stimulation signal to a tissue sample 710 via an electrode 722. An electrode 724 transmits the generated signal from the tissue sample 710 to the signal recorder 714. In this example, the signal recorder 714 includes low-noise amplifier (LNA) 732, a variable gain amplifier (VGA) 734, a filter 736, an analog to digital converter (ADC) 738, and a digital signal processor (DSP) 740. The stimulation artifact is estimated and an estimated stimulation artifact 750 may be stored in a memory. The estimated stimulation artifact 750 is subtracted from the recorded signal in the DSP 740. The signal recorder 714 in the system 700, however, cannot record signals at the times of stimulation, i.e., no concurrent stimulation and recording is supported, mainly due to the saturation of the recording system. The stimulation artifact that appears at the input of the signal recorder 714 may be a large magnitude signal. The large magnitude signal can saturate the recording system due to the large gain that is needed in the recording system to boost the small signal levels. Once the system is saturated, it is very hard or impossible to cancel the artifact effect.

Figure 8:
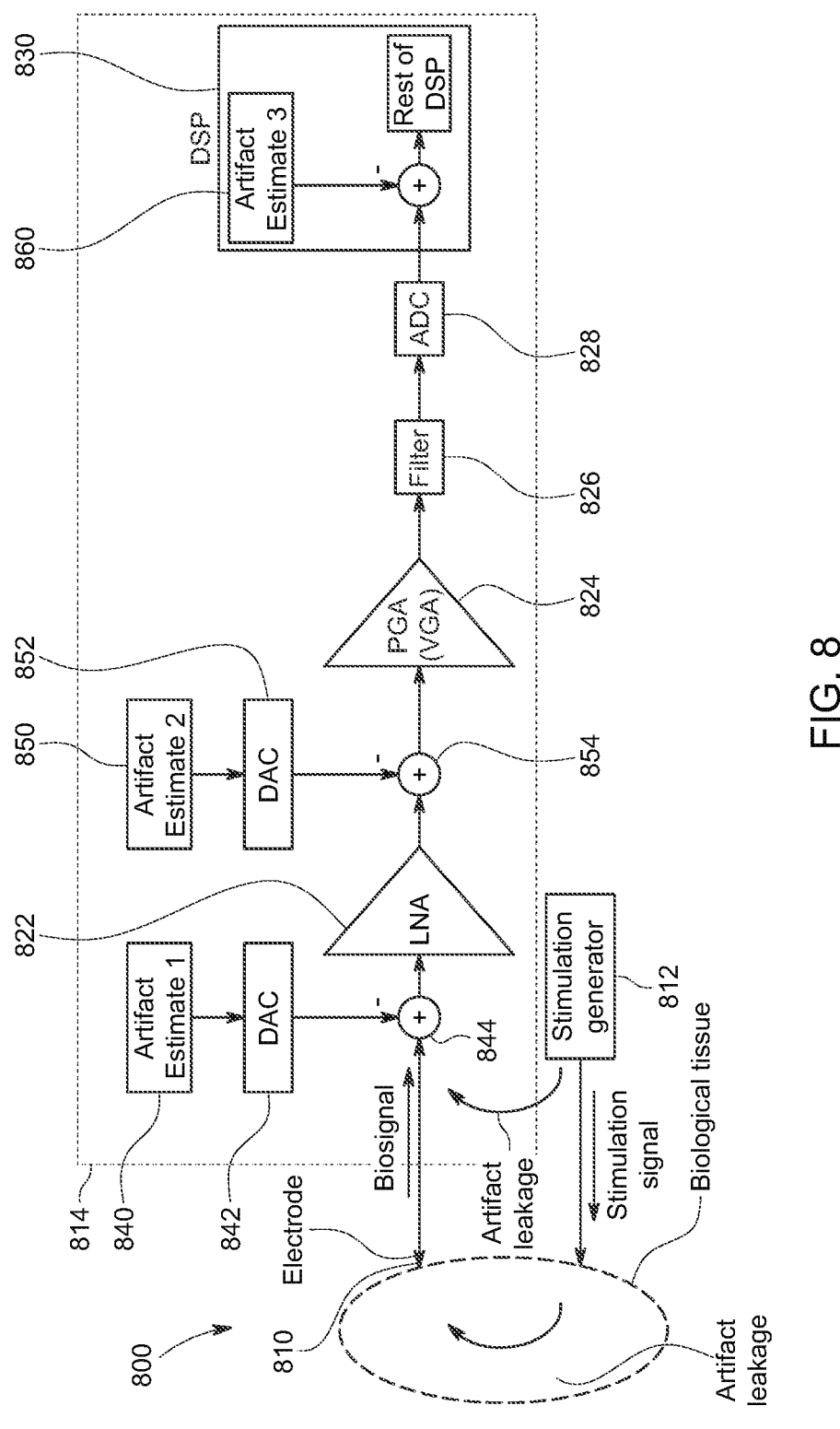
FIG. 8 illustrates a functional architecture of an example stimulation signal generator and a signal recorder with artifact cancellation in three points along the recording path according to one or more embodiments of the present disclosure.

The present disclosure is related to a technique to cancel the stimulation artifact at one or multiple points in the recording system and thus allow concurrent stimulation and recording. FIG. 8 shows the block diagram of an exemplary embodiment of a stimulation and recording system 800 that employs the example technique that cancels the artifact at three points in the signal recording circuitry. The stimulation and recording system 800 includes a stimulating signal generator 812 and a signal recorder 814. The signal recorder 814 receives a generated signal from the tissue sample from an electrode 810 and cancels the artifact. The signal from the electrode 810 is fed into a low-noise amplifier (LNA) 822, a variable gain amplifier (VGA) 824, a filter 826, an analog to digital converter (ADC) 828, and a digital signal processor (DSP) 830. The stimulation artifact is estimated and subtracted from different stages in the signal recorder 814.

In this example, a first estimation or approximation of the artifact (Artifact Estimate 1) 840 is subtracted from the contaminated signal before the signal is fed to the LNA 822. A digital-to-analog converter (DAC) 842 may be used to convert the digital representation of the artifact estimation into an analog waveform to be subtracted from the signal via subtraction logic 844 to cancel the artifact. Since the cancellation may not be perfect, a residual artifact may still be present after the first-point cancellation. Hence, after the signal is output by the LNA 822, a second-point cancellation may be introduced to subtract a second estimate of the residual artifact (Artifact Estimate 2) 850 from the contaminated signal via subtraction logic 854. This provides further attenuation of the artifact. A digital-to-analog converter (DAC) 852 may be used to convert the digital representation of the artifact estimation into an analog waveform to be subtracted from the signal. Any remaining artifact may be canceled in the DSP 830 by subtraction of a third estimate of the remaining artifact (Artifact Estimate 3) 860. The example system 800 allows for an uninterrupted recording of the desired biosignal, while canceling the artifact, and maintaining the biosignal integrity throughout the amplification and digitization stages of the system 800.

The system 800 operates in two phases. In the first phase, the artifact is estimated while in the second phase, the artifact estimation is used to cancel the artifact in the input signal. In the first phase, several measurements over time may be conducted to improve the accuracy of estimation. The stimulations and corresponding artifacts remain intact while random signals that appear at the input of the LNA 822 average out. Since the artifact is estimated when the electrodes are implanted in the tissue, a correlated neural signal may be induced by the stimulation signal. The evoked neural response usually happens with a delay (~1 ms) following the stimulation signal. If the artifact voltage settles within 1 ms, there is little temporal overlap with such correlated signals. Nonetheless, there may be scenarios that the artifact waveform does not settle for at least a few ms after the stimulation pulse, such as during a slow discharge of the residual charge on the stimulation electrode. This necessitates quantization and storage of the artifact waveforms for a longer duration which can potentially include the desired evoked neural responses. In such scenarios, a reduced stimulation signal (e.g. four times less than the intended intensity) that does not excite the nearby tissue may be applied during the artifact estimation phase. Then, during the normal system operation, assuming that the tissue behaves as a linear system, the estimated artifact can be scaled up with the same proportion as the stimulation signal.

The artifact may be estimated in different ways for input into the various stages of the signal recorder 814 in FIG. 8. One approach to estimate the artifact is the direct measurement of the artifact waveform at the target cancellation points and subtracting the direct measurement from the received signal to cancel the artifact, as shown in another example simulation system 900 in FIG. 9.

In FIG. 9, an artifact leakage component 910 of the signal input to the LNA 822 of the signal recorder 814 in FIG. 8 is sent to an analog to digital converter 920. The received artifact is converted to a digital value by the ADC 920 and stored in a memory 922. The stored artifact value is then fed into the DAC 842 and the output of the DAC 842 is subtracted from the signal input to the LNA 822 via the subtraction logic 844. This is an open-loop approach with limited accuracy and precision.

Figure 10:
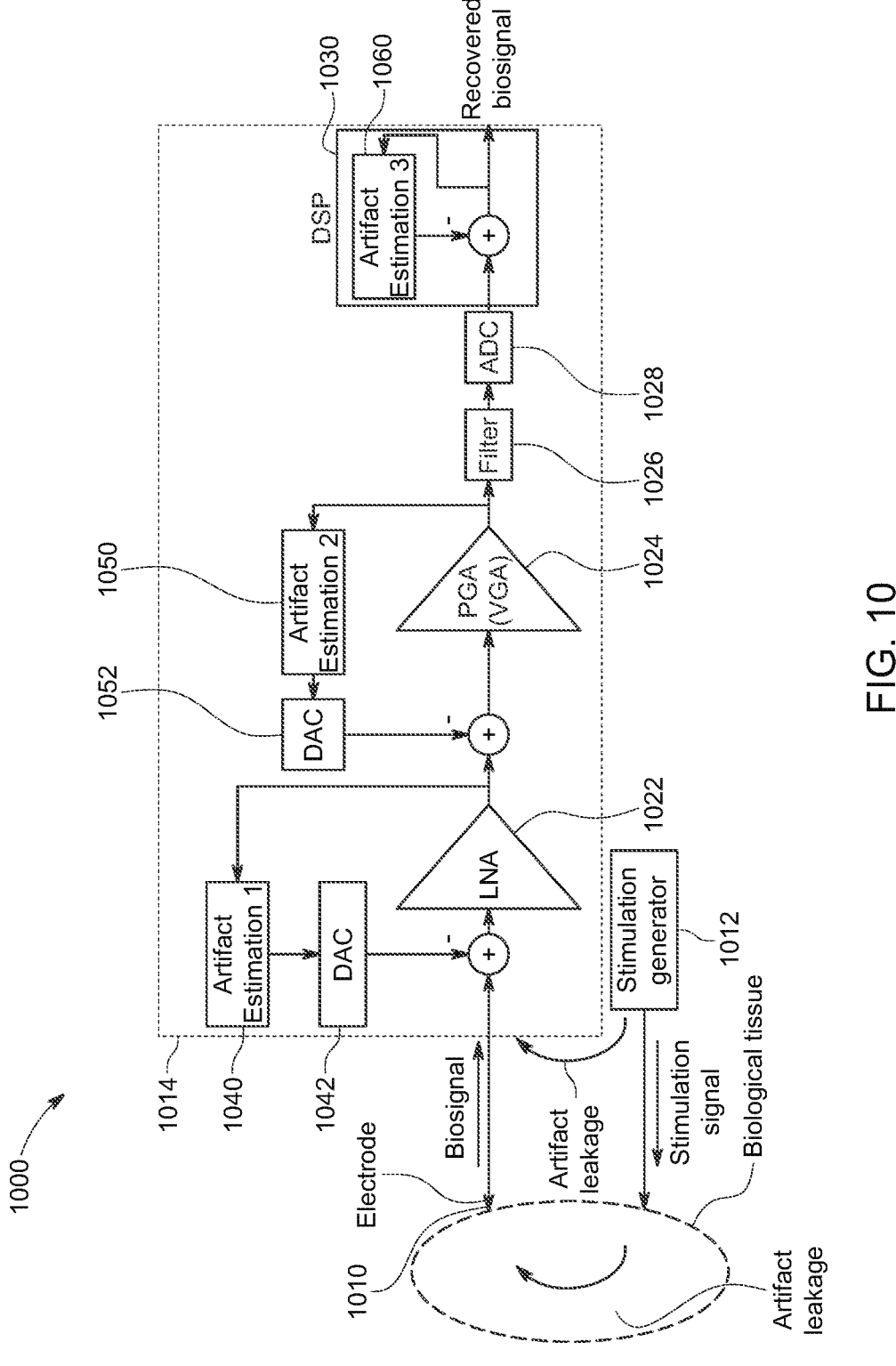
FIG. 10 illustrates an example functional architecture of a stimulation signal generator and a signal recorder with closed-loop artifact estimation and cancellation in three points along the recording path according to one or more embodiments of the present disclosure.

Another approach is a closed-loop artifact estimation that can provide a more accurate and precise estimate of the artifact. In a closed-loop, the output of the loop (subtracted signal) will be reduced over time as a better estimate of artifact is derived. Moreover, in the open-loop artifact estimation, the ADC that is directly connected to the front-end or the recorder may satisfy challenging constraints such as a very low input capacitance to avoid loading the high-impedance node where the recording electrode is connected to. FIG. 10 shows an example system 1000 with 3-point closed-loop artifact estimation and cancellation incorporated in another example stimulation system 1000. The system 1000 includes a stimulating signal generator 1012 and a signal recorder 1014. The signal recorder 1014 receives a generated signal from the tissue sample from an electrode 1010. The signal from the electrode 1010 is fed into a low-noise amplifier (LNA) 1022, a variable gain amplifier (VGA) 1024, a filter 1026, an analog to digital converter (ADC) 1028, and a digital signal processor (DSP) 1030. The stimulation artifact is estimated and subtracted from different stages in the signal recorder 1014 through three different closed-loop feedbacks.

In this example, a first estimation or approximation of the artifact 1040 (Artifact Estimate 1) is estimated from the output of the LNA 1022 and fed back to a digital-to-analog converter (DAC) 1042. The DAC 1042 may be used to convert the digital representation of the artifact estimation into an analog waveform to be subtracted from the input signal to the LNA 1022. A second feedback cancellation may be estimated from the output of the PGA 1024 to subtract a second estimate of the residual artifact 1050 (Artifact Estimate 2) from the contaminated signal. The output artifact is fed into a digital-to-analog converter (DAC) 1052 may be used to convert the digital representation of the artifact estimation into an analog waveform to be subtracted from the signal input to the PGA 1024. A third feedback cancellation may be estimated by the output of the DSP 1030 resulting in a third estimation of the artifact 1060 (Artifact Estimate 3). The estimation 1060 is fed back and subtracted from the input of the DSP 1030.

Figures 11A, 11B:
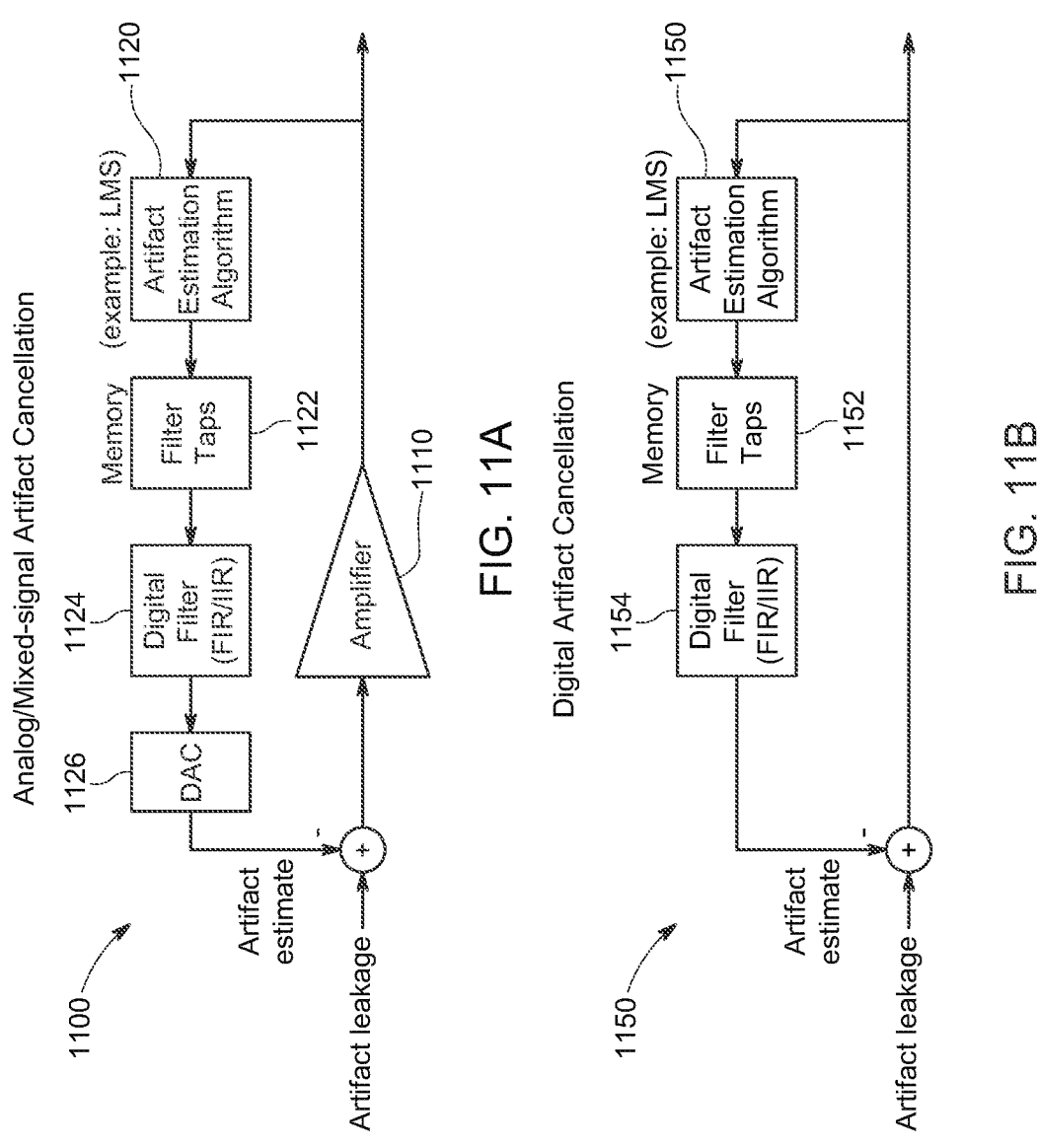
FIG. 11A shows an example analog cancellation implementation of the artifact estimation using a least mean square algorithm according to one or more embodiments of the present disclosure.
FIG. 11B shows an example digital cancellation implementation of the artifact estimation using a least mean square algorithm according to one or more embodiments of the present disclosure.

Different algorithms may be used to estimate artifacts at the points of cancellation in recording circuitry such as the signal recorder 812 of the system 800 in FIG. 8. For instance, a least-mean-square (LMS) algorithm may be used to train the coefficients or taps of a finite-impulse-response (FIR) or infinite-impulse-response (IIR) filter to estimate the artifact by minimizing the residual artifact at each cancellation stage. FIG. 11A shows an example circuit 1100 using analog cancellation implementation of the artifact estimation using LMS. FIG. 11B shows an example circuit 1150 using digital cancellation implementation of the artifact estimation using LMS. Both of the circuits 1100 and 1150 in FIGS. 11A-11B use closed-loop artifact estimation and a cancellation stage to cancel the artifact. Multiples of these stages may be cascaded to offer additional artifact cancellation.

The circuit 1100 in FIG. 11A inputs the output signal from an amplifier 1110 to an artifact algorithm 1120 that employs LMS to determine the estimation of the artifact. The LMS algorithm tries to estimate the filter coefficients (or taps) such that the filter output mimics the artifact waveform. This estimation happens dynamically in successive cycles to minimize the mean-square of the error between the actual artifact and its replica reproduced by the filter. The resulting estimation of the artifact is sent to a memory 1122 for application to filter taps. The LMS algorithm when used as the artifact algorithm 1120 finds the optimum coefficients for the digital filter 1124. The LMS algorithm outputs the calculated coefficients, which are fed into the subsequent filter 1124. The filter output is a digital estimate of the artifact waveform, which is converted to an analog estimate by the DAC 1126. The filter taps are used to adjust a digital filter 1124. In this example, the filter 1124 may be based on a finite-impulse-response (FIR) or infinite-impulse-response (IIR) filter. The output of the filter 1124 is fed into a DAC 1126 that outputs an analog signal of the artifact estimation. The artifact estimation signal is then subtracted from the input to the amplifier 1110.

The circuit 1150 in FIG. 11B inputs a value of the signal to an artifact algorithm 1120 that employs LMS to determine the estimation of the artifact as a component of the signal. The estimation follows the process of the corresponding analog estimate explained above. The resulting artifact estimation is sent to a memory 1152 as taps for filters. In this example, the filter taps stored in the memory 1152 are used to adjust a digital filter 1154. In this example, the digital filter 1154 may be based on a finite-impulse-response (FIR) or infinite-impulse-response (IIR) filter. The output of the filter 1154 is the artifact estimation and is subtracted from the signal.

Figure 12A:
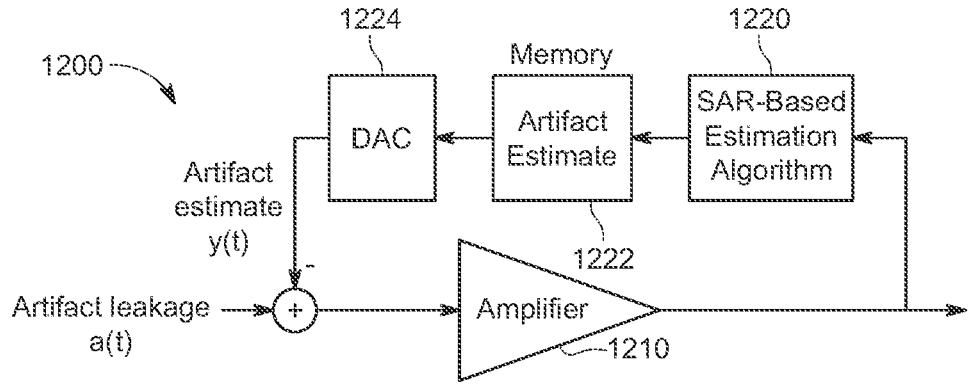
FIG. 12A illustrates a functional architecture of a successive-approximation-register (SAR) based artifact estimation and cancellation stage according to one or more embodiments of the present disclosure.

Artifact estimation may be made by a successive-approximation-register (SAR) algorithm, as shown in another example circuit 1200 in FIG. 12A. The circuit 1200 inputs the output signal from an amplifier 1210 to an artifact algorithm 1220 that employs a SAR-based method to determine the artifact estimation. The resulting estimation of the artifact is sent to a memory 1222. The estimated value of the artifact in the memory 1222 is fed into a DAC 1224 that outputs an analog signal of the artifact estimation. The artifact estimation signal is then subtracted from the input to the amplifier 1210.

Figure 12B:
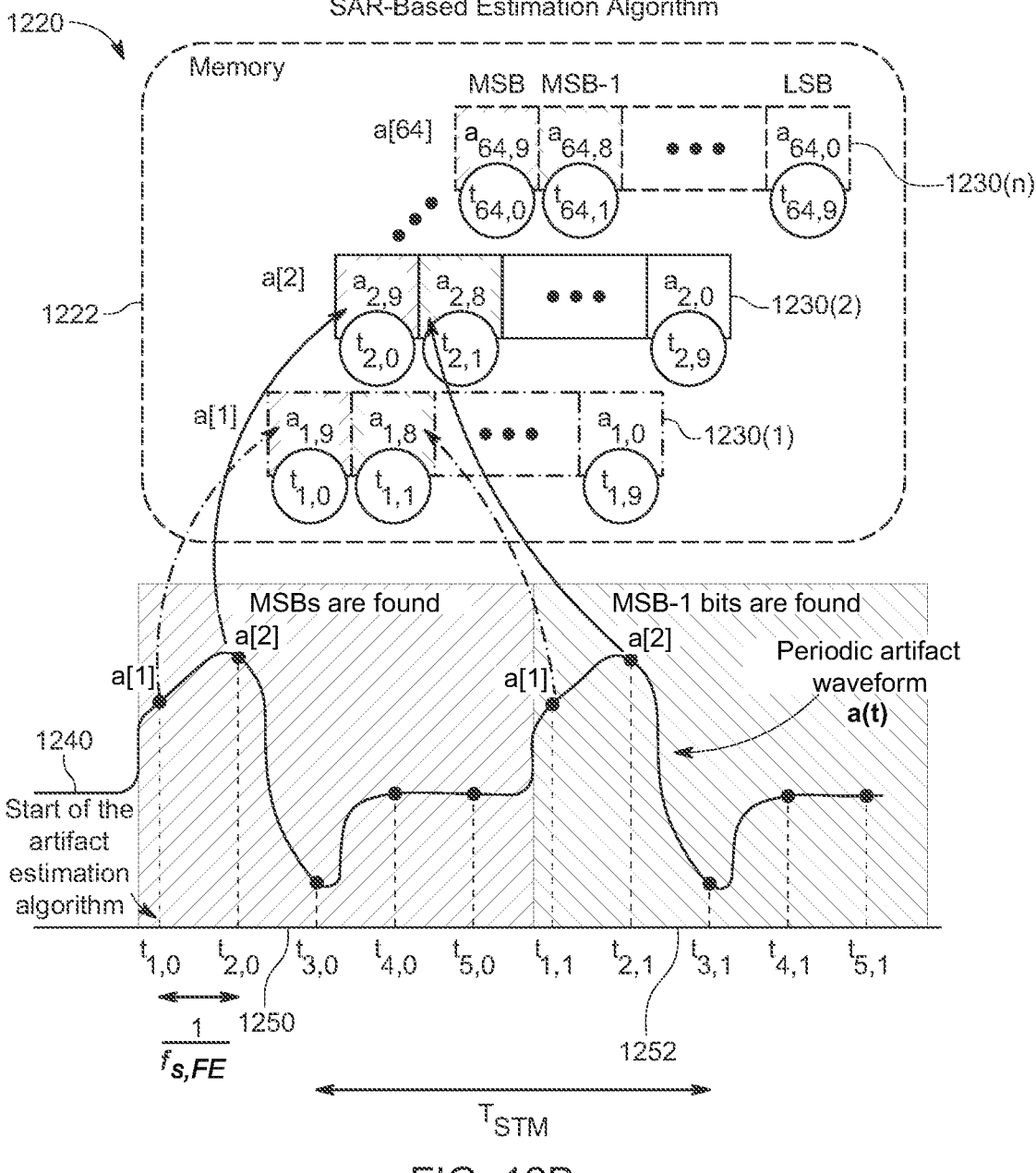
FIG. 12B shows a process of the SAR-based algorithm in FIG. 12A according to one or more embodiments of the present disclosure.

The process of data collection for the SAR algorithm is shown in FIG. 12B. The memory 1222 includes a series of 10 bit samples of the residual artifact 1230(1) to 1230(n) that are obtained from periodic sampling. Each of the samples includes a certain number of bits, such as ten bits, arranged from most significant bit to least significant bit for each sample. In this example, 64 samples of the residual artifact are stored, but other numbers of estimations may be used for the SAR algorithm depending on the length of the artifact. Thus, an artifact that is relatively short may allow less than 64 samples, while relatively long artifacts may require more than 64 samples. The estimation phase collects data to apply the SAR algorithm 1220 to provide an artifact estimation.

At the beginning of the estimation phase, a front-end continuous-time (CT) estimation loop is enabled, while a back-end discrete-time (DT) loop is disabled. During an estimation phase, a desired stimulation signal is periodically applied to the tissue, which creates a periodic artifact waveform 1240 a(t). In a first stimulation cycle 1250, a comparator detects the signs of the consecutive samples of the artifact (a[1], a[2], . . . , a[64]) and determines the status of the most significant bit (MSB) of each N-bit sample (a[1,N–1], a[2,N–1], etc.) 1230(1)-1230(n), for example, ($a_{1,9}$, $a_{2,9}$, . . . , $a_{64,9}$). Thus, the period of the stimulation cycle multiplied by the sampling rate (fs, FE) constitutes the estimation phase.

The maximum memory storage is dedicated to the 64 samples at this cancellation stage in this example. The respective most significant bits are stored in the samples 1230(1)-1230(n). During a second stimulation cycle 1252, an N-bit, for example 10 bit, capacitive DAC (CDAC)

reconstructs the first estimate of the artifact (which only includes the MSB of the samples) and subtracts it from the received artifact. The LNA amplifies the estimation error and feeds it back to the comparator to determine the MSB-1 bits (a[1,N–2], a[2,N–2], etc.), for example, ($a_{1,8}$, $a_{2,8}$, . . . , $a_{64,8}$). The respective MSB-1 bits are stored in the samples 1230(1)-1230(n). This loop operates for N stimulation cycles, for example 10 stimulation cycles, to determine all the N bits, for example 10 bits, of the artifact samples 1230(1)-1230(n).

Figure 13:
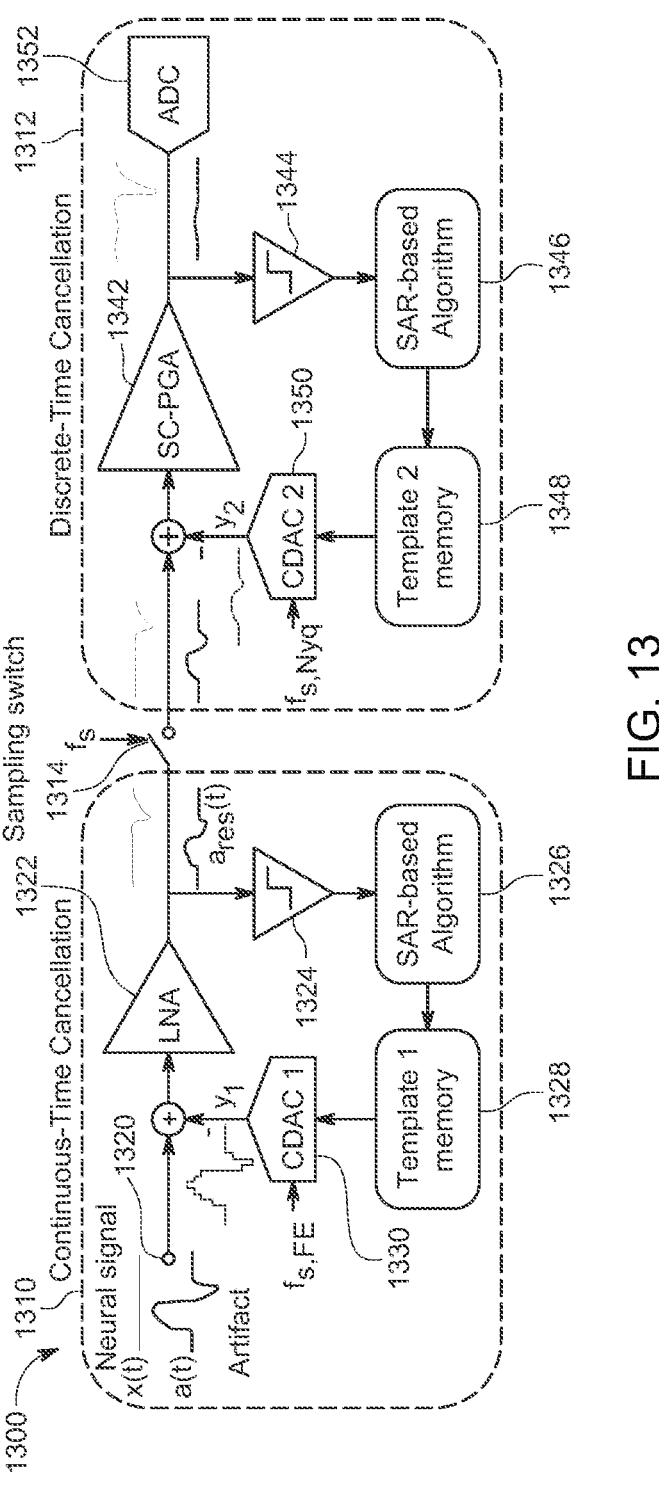
FIG. 13 illustrates an example of a two-point cancellation scheme according to one or more embodiments of the present disclosure.

The multi-point artifact cancellation technique can be implemented in the continuous-time (CT) domain, the discrete-time (DT) domain, or a combination of both. FIG. 13 illustrates an example of a two-point cancellation system 1300 where the first-point cancellation happens in the continuous-time (CT) domain and the second-point cancellation happens in the discrete-time (DT) domain. The system 1300 includes a first CT stage 1310 and a second DT stage 1312. Thus, the second stage 1312 operates in the discrete-time (DT) domain. The second stage 1312 is coupled to the first stage 1310 via a sampling switch 1314. The first stage 1310 accepts an input signal 1320 that includes the neural signal and the artifact. The input signal 1320 is fed into an LNA 1322. The signal is initially input to a comparator 1324 and fed into an SAR based algorithm 1326 similar to the algorithm described in FIG. 12A-12B. The SAR algorithm 1326 produces a first template 1328 that is stored in a memory. The template 1328 is used by a capacitive DAC 1330 to produce an artifact estimation that is subtracted from the input signal 1320 via subtraction logic. Thus, the first stage 1310 estimates the artifact waveform a(t) and subtracts a coarse approximation of the artifact (y1) from the received signal at the input of the low-noise amplifier (LNA) 1322. The residual artifact thus is amplified in the continuous-time (CT) domain, low-pass filtered and sampled, for example, at the Nyquist rate ($f_{s,Nyq}$=19.5 kS/s) by the sampling switch 1314.

The second stage 1312 accepts the output signal from the first stage 1310 that includes the neural signal and a residual of the artifact. The output signal is fed into a switched capacitor programmable gain amplifier (SC-PGA) 1342. The signal output from the SC-PGA 1342 is filtered via a filter 1344 and fed into a SAR based algorithm 1346 similar to the algorithm described in FIGS. 12A-12B. The algorithm 1346 produces a second template 1348 that is stored in a memory. The second template 1348 is used by a capacitive DAC 1350 to produce an artifact estimation that is subtracted from the signal input to the SC-PGA 1342 via subtraction logic. The residual artifact in each contaminated sample is estimated (y2) and subtracted from the sampled signal at the input of the SC-PGA 1342. The output signal is then sent to an analog to digital converter 1352. Consequently, the output of the SC-PGA 1342 carries the samples of the amplified neural signal with minimal amount of residual artifact to the analog to digital converter (ADC) 1352 for quantization. In this example the ADC 1352 is a 10 bit successive-approximation register (SAR) ADC. During the signal acquisition phase after the estimation phase, both the estimation loops are disabled, while the first CDAC 1330 and the second CDAC 1350 cancel the artifact at two points along the signal amplification chain.

A continuous-time (CT) estimation loop is contained in the first CT stage 1310 while a discrete-time domain loop is contained in the second DT stage 1312. The first stage estimates the artifact waveform a(t) and subtracts a coarse approximation of the artifact (y1) from the received signal at the input of the low-noise amplifier (LNA) 1322. The residual artifact is subsequently amplified in the continuous-time (CT) domain, low-pass filtered and sampled by the sampling switch (at the Nyquist rate) 1314 which takes the signal to the discrete-time (DT) domain. The residual artifact in each contaminated sample is estimated (y2) and subtracted from the sampled signal at the input of the switched-capacitor programmable-gain amplifier (SC-PGA) 1342. Consequently, the output of the SC-PGA 1342 carries the samples of the amplified neural signal with minimal amount of residual artifact to the 10-bit successive-approximation register (SAR) ADC 1352 for quantization. Moving from continuous-time to discrete-time signal conditioning allows for time-sharing the second-point cancellation and ADC among multiple recording channels.

Thus, the example SAR estimation algorithm process in FIG. 12B may be used in the artifact cancellation points at the input of the LNA 1322 and the input of the SC-PGA 1342. Comparing FIG. 12B and FIG. 13, the memory block 1222 in FIG. 12B corresponds to the template memories 1328 and 1348 shown in FIG. 13. The CDAC 1330 and CDAC 1350 convert the digital output of the memories 1328 and 1348 respectively into an analog waveform to replicate the artifact waveform.

Figure 14A:
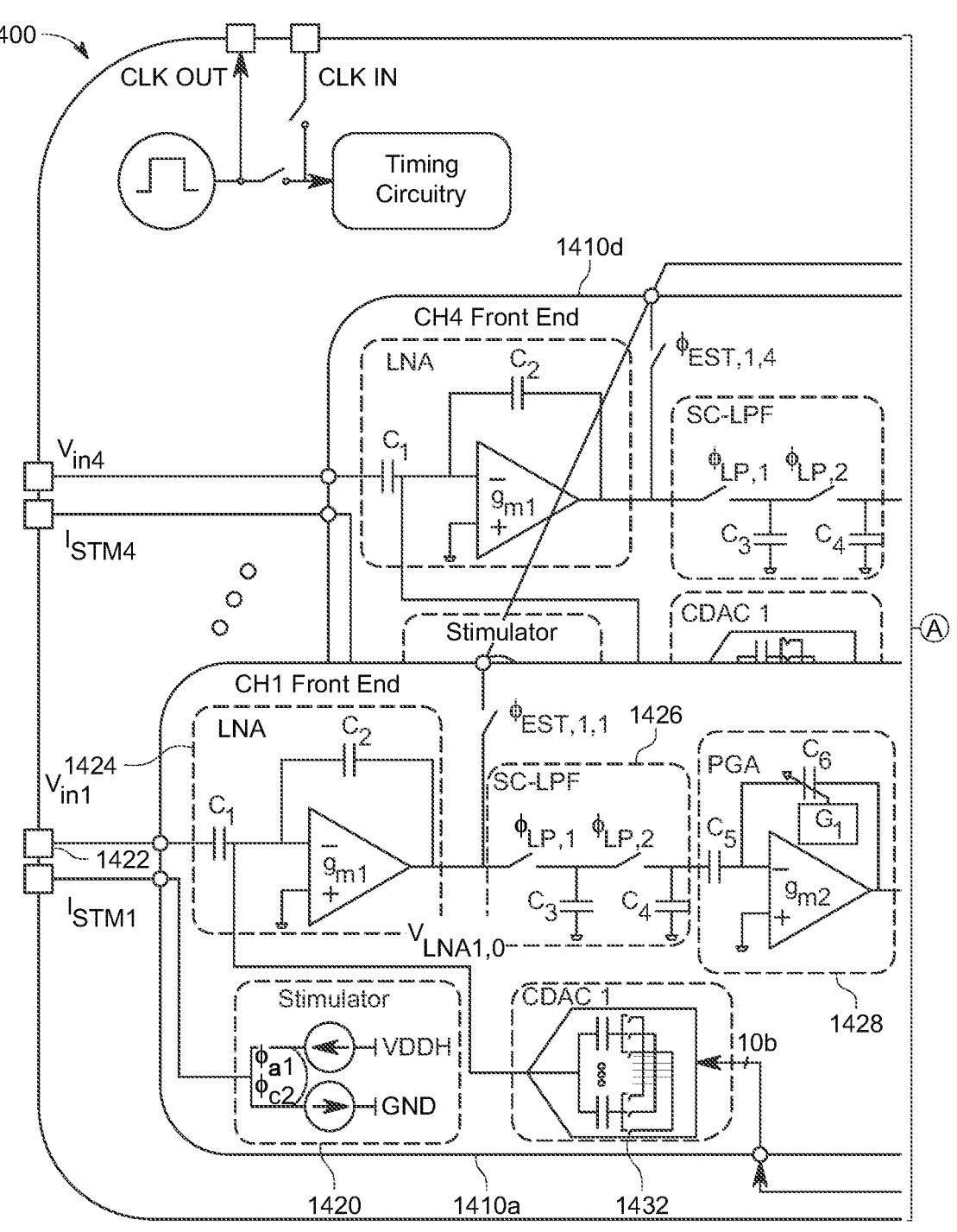
FIG. 14A illustrates a block diagram of an example stimulation and recording circuit employing multi-point cancellation scheme using the SAR-based algorithm according to one or more embodiments of the present disclosure.

FIG. 14A shows a block diagram of an exemplary neural interface circuit 1400 with four recording and four simulation channels that utilizes the two-point continuous-time (CT) and discrete-time (DT) stimulation artifact cancellation scheme described herein. In this example, each of the four channel front end circuits 1410a-1410d can be connected to electrodes that are placed on the tissue sample of interest. The four channels provide different ways of measurement at their interface with the tissue. For example, the four channels may be configured for one recording electrode and no stimulation electrode; one stimulation electrode and no recording electrode; one stimulation electrode and one recording electrode; and one electrode shared between the recording and stimulation blocks in the circuit 1400. The circuit 1400 includes four parallel recording and stimulation circuits 1410a, 1410b, 1410c, and 1410d that constitute the front end of the circuit 1400. The outputs of the recording and stimulation circuits 1410a-1410d are coupled to a shared back-end circuit 1412. A SAR artifact estimation and cancellation module 1414 provides offset estimations for artifact cancellation. A SAR offset circuit 1416 is coupled to the outputs of each of the recording and stimulation circuits 1410a-1410d. Although four channels are shown, different numbers of channels may be used that apply the cancellation of artifacts described herein.

Each of the front end recording and stimulation circuits 1410a-1410d are identical and thus the following description of the front end recording and stimulation circuit 1410a applies to the other front end circuits. The front end recording and stimulation circuit 1410a includes a stimulator 1420 that provides a stimulation signal through an electrode to a tissue sample. A received signal from the tissue may be read via a signal receiver input 1422. The signal from the receiver input 1422 is fed into a LNA 1424. The output of the LNA 1424 is coupled to a switchable capacitance low pass filter (SC-LPF) 1426. The output of the low pass filter 1426 is coupled to a programmable gain amplifier (PGA) 1428. The output of the amplifier 1428 is coupled to a unity-gain voltage buffer 1430. The front end recording and stimulation circuit 1410a also includes a capacitive DAC 1432 that provides an artifact cancellation signal to the input signal to the LNA 1424.

The outputs of the four front-end recording and stimulation circuits 1410a-1410d are time-multiplexed into the shared back end circuit 1412. The DC offset of the voltage buffers 1430 in each recording and stimulation circuit 1410a-1410d is calibrated using a SAR-based algorithm in the SAR offset circuit 1416 which controls a switch bank to provide the output of a shared current DAC 1434 at the input to the back end circuit 1412 to the outputs from the multiplexed outputs of the recording and stimulation circuits 1410a-1410d.

The output signals from the front end recording and stimulation circuits 1410a-1410d are coupled to a cascade of a first switched capacitor programmable gain amplifier (SC-PGA) 1440 and a second SC-PGA 1442. The output of the two cascaded stages of switched capacitor amplifiers such as the SC-PGAs 1440 and 1442 amplify the DT signal and drive a 10 bit SAR ADC 1444. The output of the SAR ADC 1444 is coupled to a serializer and packetizer circuit 1446. The back end circuit 1412 includes a capacitive DAC 1448 that provides an artifact cancellation signal to the input signal to the SC-PGA 1440.

In this example, output signals from the LNA 1424 from each of the recording stimulation circuits 1410a-1410d are input to the SC-PGA 1440 of the back end circuit 1412. The output of the SC-PGA 1440 is input into the artifact estimation and cancellation module 1416 during an artifact estimation phase. The artifact from the input signal is buffered and compared via a comparator 1450 by the artifact estimation and cancellation module 1416. A comparator offset circuit 1452 adjusts the output of the comparator 1450. The output is fed into SAR-based artifact estimation logic 1454 as explained above.

The SAR estimation and cancellation module 1416 estimates and stores the differential-mode (DM) artifact data for each of the four channels in a memory block 1460. The SAR estimation and cancellation module 1416 also estimates and stores the common-mode (CM) artifact data for each of the four channels in a memory block 1462. The SAR estimation and cancellation module 1416 also stores the residual artifact data corresponding to the output at each of the four channels in a memory block 1464. The data from the memory blocks 1460 and 1462 are read by artifact reconstruction logic 1466 to produce an artifact estimation for the CDAC 1432 for canceling the artifact component of the input signal to the LNA 1424. The data from the memory block 1464 is read by the CDAC 1448 to cancel the discrete-time DM artifact component of the input signal to the SC-PGA 1440.

In an example of a chip with the system 1400, the chip is fabricated in a 0.18 μm complementary metal oxide semiconductor (CMOS) technology, consumes 0.35 mm$^2$ of area and 5.2 μW of power per recording channel. The chip includes the amplification stages and CDACs 1432 for each of the four channels, the CDAC 1448, and the ADC 1444. In this example, the cancellation digital circuits (including the SRAM-based memory blocks 1460, 1462, and 1464) consume 2.7 μW per channel. All the blocks are driven from a 1V supply, except the stimulator 1420 and the CDAC 1432, which are operated with a 3V supply. In this example, the recording chain has a maximum gain of 75.3 dB, and integrated input-referred noise of 9.8 $\mu V_{rms}$ in a bandwidth of 10 Hz-9 kHz. The example chip is implemented fully differentially across all the gain, cancellation, and quantization stages.

Figure 14B:
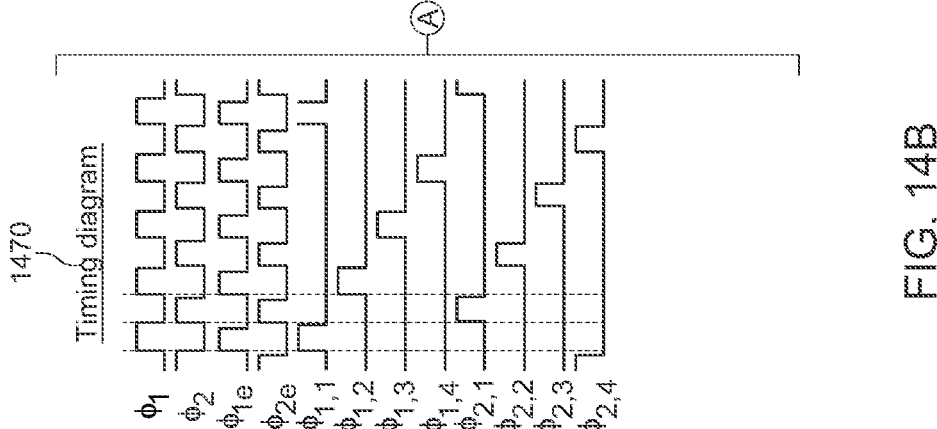
FIG. 14B illustrates timing diagrams of the cancellation process applied to an input signal to the example stimulation and recording circuit in FIG. 14B according to one or more embodiments of the present disclosure.

FIG. 14B shows a timing diagram and the simulated sequential operation of the estimation and cancellation algorithm operated by the circuit 1400. FIG. 14B shows the sequential estimation and cancellation of a stimulation artifact input on the first channel of a signal (Vin1) input to the recording and stimulation circuit 1410*a*. The input signal has the artifact that has CM and DM components, which are canceled by the circuit 1400.

A timing diagram 1470 shows the different channel selection signals applied to the circuit 1400. A first voltage trace 1472 shows the common-mode component of the input signal. A second voltage trace 1474 shows the differential-mode component of the input signal. A voltage trace 1476 shows the output of the LNA 1424 while a voltage trace 1478 shows the output of the SC-PGA 1440.

The data for determining the artifact estimations is collected through channel selection determined by the signals in the diagram 1470. Thus, a first phase 1480 allows the system to collect readings for CM artifact estimation for the first channel. A second phase 1482 allows collection of data for DM artifact estimation for the first channel. The first and second phases 1480 and 1482 are repeated for each of the three other channels for determining the respective CM artifact estimation and DM artifact estimation for the channels. After the first and second phases are performed for the four channels, a third phase 1484 allows collection of data for discrete-time DM artifact estimation for all channels. In the third phase 1484, a first sample is taken from each channel sequentially, followed by a second sample until the desired number of samples are collected for each sample. The estimation phases may be repeated when there is a change to the stimulation signal such as in frequency and/or intensity. Also, the electrode-tissue interface properties may change over time and therefore, the artifact may need to be estimated periodically during the operation of the stimulation-recording interface in the biological tissue, to account for the time-variability of the stimulation artifact. After the third phase 1484, the artifacts are canceled on both the output signal from the LNA 1424 via subtraction logic as shown by the trace 1476 and the output signal from the SC-PGA 1440 as shown by the trace 1478.

In general, the stimulation artifact that is coupled to the differential inputs to the front end recording and stimulation circuit 1410*a*-1410*d* has both common-mode (CM) and differential-mode (DM) components. The CM component can readily reach several hundreds of mV, perturb the biasing of the transconductance cell of the LNA 1424, and degrade the linearity of the signal. This necessitates the mitigation of the CM artifact in the front end circuits 1410*a*-1410*d* in addition to cancelling the DM artifact.

Figure 15A:
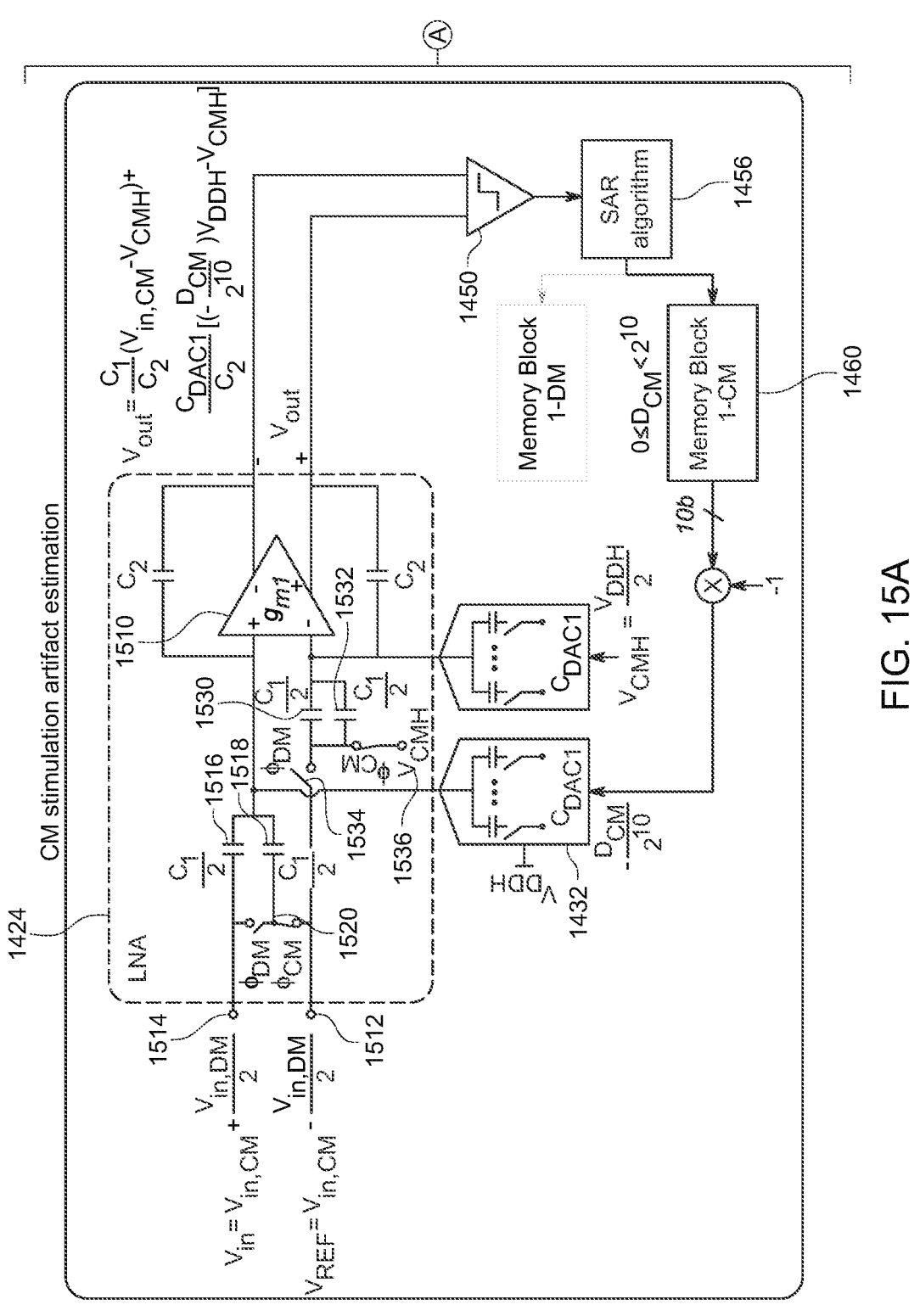
FIG. 15A illustrates a detailed circuit diagram of the components that perform common-mode (CM) and differential-mode (DM) artifact estimation and cancellation of the circuit in FIG. 14A according to one or more embodiments of the present disclosure.

To mitigate the CM artifact and cancel the DM artifact, the LNA 1424 includes different transmission gate switches to allow switching between DM and CM sensing of the incoming artifact. FIG. 15A is a detailed circuit diagram of the LNA 1424 in FIG. 14A in a CM stimulation artifact estimation mode and a DM stimulation artifact estimation mode. The LNA 1424 includes a gain circuit 1510 that has a first input that is coupled to a voltage reference 1512 and a signal input 1514. The signal input 1514 is derived from the sample and is coupled to a capacitor 1516 to the first input of the gain circuit 1510. The voltage reference input 1512 is coupled to a capacitor 1518 to the first input of the gain circuit 1510. A transmission gate switch 1520 is coupled between the capacitors 1516 and 1518 to either directly connect the reference voltage 1512 through to the first input of the gain circuit 1510 or connect the input 1514 through both capacitors 1516 and 1518. The other input of the gain circuit 1510 is connected to two parallel capacitors 1530 and 1532. A transmission gate switch 1534 may be switched to allow the reference voltage 1512 to be directly connected to the other input of the gain circuit 1510 through the capacitors 1530 and 1532 or to a voltage reference (VCMH) 1536. In this example, the VCMH voltage reference 1536 is a fixed bias voltage (1.5V) at half the DAC full-scale voltage (3V). As shown in FIG. 15A, the output of the CDAC 1432 is coupled to both inputs of the gain amplifier 1510.

Using the same SAR-based algorithm discussed herein, the CM component is initially estimated and stored during the first phase ($\phi_{CM}$) 1480 in FIG. 14B, which is followed by the DM artifact estimation during the second phase ($\phi_{DM}$) 1482 while the CM artifact cancellation is enabled.

Referring to FIG. 15A, the first-point cancellation includes both a differential-mode (DM) and a common-mode (CM) artifact estimation and cancellation circuitry or logic coupled to the LNA 1424 in FIG. 14A. In the common-mode estimation and cancellation circuitry, the input voltage source 1514 is input through the capacitor 1516 to the input of the gain circuit 1510. The gate switch 1520 is switched to connect the reference voltage input 1512 through the capacitor 1516 to the input of the gain circuit 1510.

In the CM configuration, the outputs of the gain circuit 1510 are coupled to the comparator 1450 and input into the SAR algorithm 1456. The output of the SAR algorithm 1456 is stored in the memory block 1460. The data in the memory block 1460 is multiplied by −1 and fed into the CDAC 1432 that functions as subtraction logic to perform CM cancellation on the input to the LNA 1424. The calculation is implemented in a two's complement binary format to accommodate both negative and positive integers.

In the DM configuration, the gate switch 1520 is switched to connect the input voltage 1514 to both of the capacitors 1516 and 1518. The resulting signal is connected to one of the inputs of the gain circuit 1510. The other input of the gain circuit 1510 is coupled to the reference voltage input 1512 by switching the gate switch 1534. The reference voltage input 1512 thus is coupled through the capacitors 1530 and 1532 to the input of the gain circuit 1510.

In the DM configuration, the outputs of the gain circuit 1510 are coupled to the comparator 1450 and input into the SAR algorithm 1456. The output of the SAR algorithm 1456 is stored in the memory block 1462. The data in the memory blocks 1460 and 1462 is fed into the artifact reconstruction logic 1466. The data in the memory block 1460 is multiplied by −1 and summed with the data in the memory block 1462. This result is fed into the CDAC 1432 that functions as subtraction logic to perform DM cancellation on one of the inputs to the gain circuit 1510. The artifact reconstruction logic 1466 also multiplies the data from the memory block 1462 by −1 and adds the result to the output of the memory block 1460 that is multiplied by −1. This result is incremented by +1 and fed into the CDAC 1432 to perform DM cancellation on the other input of the gain circuit 1510.

Figure 15B:
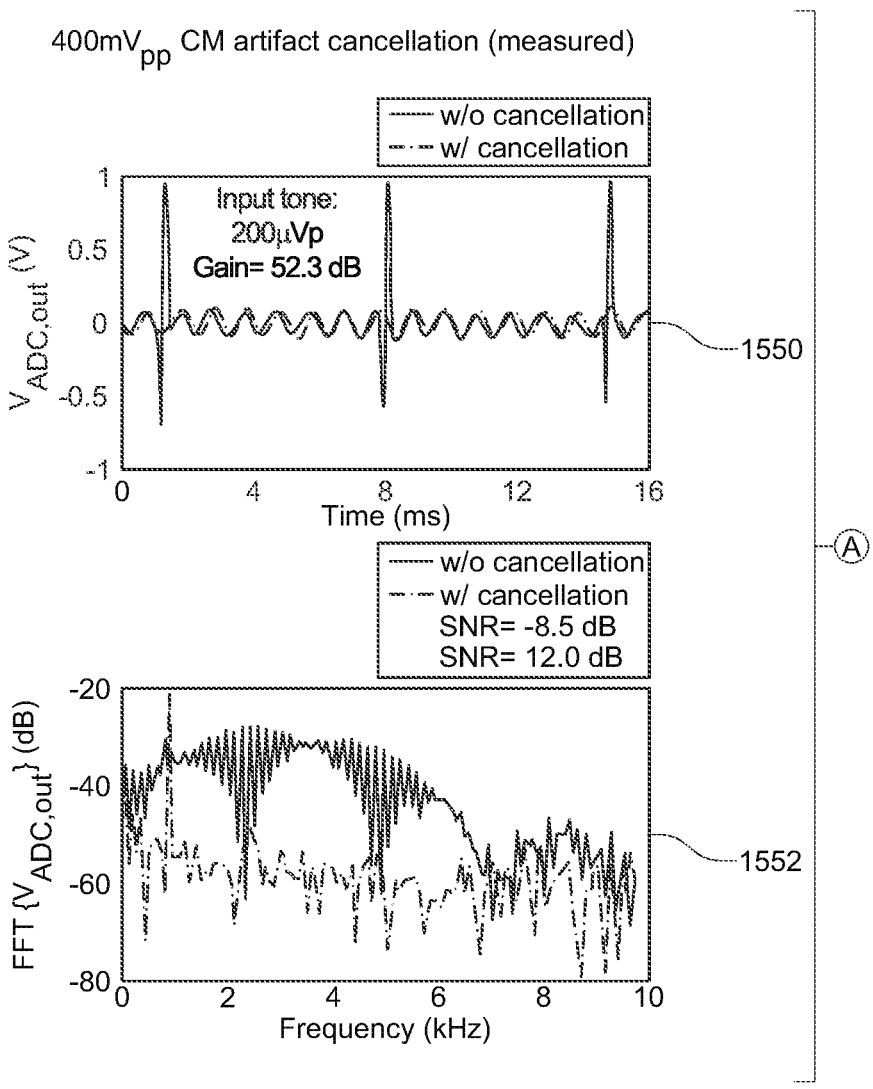
FIG. 15B shows different graphs of measured results of the CM and DM estimation and cancellation from the circuits in FIG. 15A according to one or more embodiments of the present disclosure.

FIG. 15B shows graphs of the measured cancellation performance in recovering a single-tone signal in the presence of CM and DM artifacts. In this example, a 200-µVp 1-kHz tone contaminated with 400-mV$_{pp}$ CM and 800-mV$_{pp}$ DM artifacts are input into the circuit 1400 in FIG. 14A. A graph 1550 plots the output voltage of the ADC 1444 in FIG. 14 with cancellation and without cancellation for an example 400-mV$_{pp}$ CM artifact. A graph 1552 plots the fast Fourier transform of the output voltage of the ADC 1444 in FIG. 14A with cancellation and without cancellation for an example 400-mV$_{pp}$ CM artifact. A graph 1554 shows the CM/DM cancellation performance for the CM and DM artifacts compared to no cancellation. A graph 1556 shows the output voltage of the ADC 1444 in FIG. 14A with cancellation and without cancellation for an example 800-mV$_{pp}$ DM artifact. A graph 1558 plots the fast Fourier transform of the output voltage of the ADC 1444 in FIG. 14A with cancellation and without cancellation for an example 800-mV$_{pp}$ CM artifact.

Figure 16A:
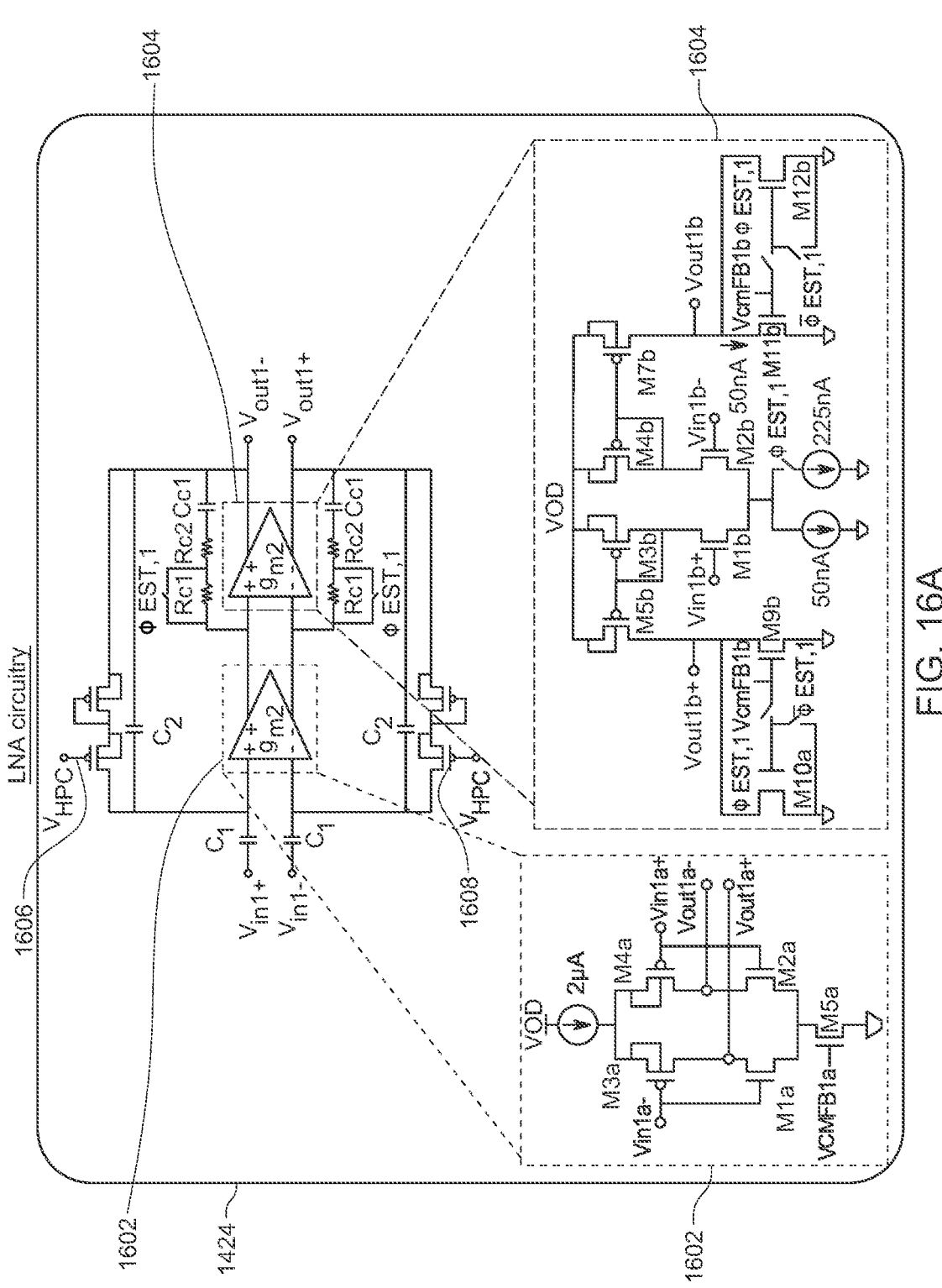
FIG. 16A illustrates a circuit diagram of the low-noise amplifier (LNA) in the system in FIG. 14A according to one or more embodiments of the present disclosure.

FIG. 16A shows a detailed circuit diagram of the LNA 1424 in FIG. 14A. The LNA 1424 includes two gain circuits 1602 and 1604. The gate switches and capacitor network in FIG. 15A are simplified and shown as input capacitors in FIG. 16A. The gain circuits 1602 and 1604 have dual inputs and dual outputs. Each of the gain circuits 1602 and 1604 are shown in detail in FIG. 16A. One input of the gain circuits 1602 and 1604 is coupled to the voltage signal from the sample. The other input is coupled to a reference voltage. A metal-oxide-semiconductor (MOS) resistor circuit 1606 and a MOS resistor circuit 1608 are provided to provide a programmable low-frequency high-pass corner for the LNA frequency response.

Figure 16B:
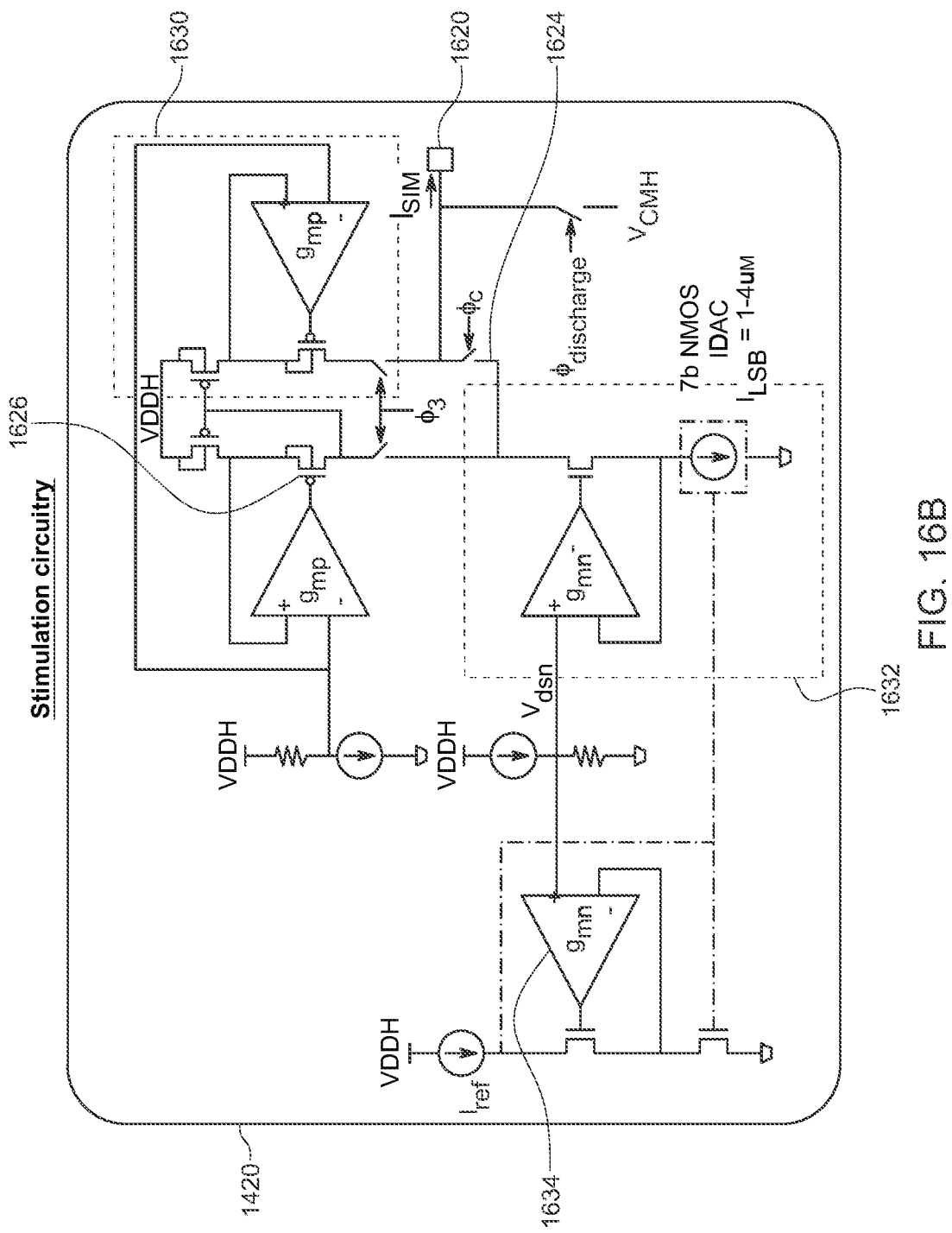
FIG. 16B illustrates a circuit diagram of the stimulation module in the system in FIG. 14A according to one or more embodiments of the present disclosure.

FIG. 16B shows a detailed circuit diagram of the stimulator 1420 in FIG. 14A. The stimulator 1420 in each of the four channels in FIG. 14A provides an output 1620 that is coupled to an electrode to stimulate the sample. The stimulation circuitry in the stimulator 1420 uses a 7-bit NMOS current DAC (IDAC) (not shown), which has a tunable least-significant bit (LSB) current of 1-4 μA. The stimulation cathodic current is directly generated from an NMOS array 1624 (phase φc) and for the anodic current, the current of the IDAC is rerouted to a PMOS mirror circuit 1626 on top (phase φa). A regulated cascode configuration 1628 is implemented for the top and bottom current sources 1630 and 1632 to boost the output impedance of the stimulator 1420. A reference current circuit 1634 is provided for the bottom current source 1632.

Figure 16C:
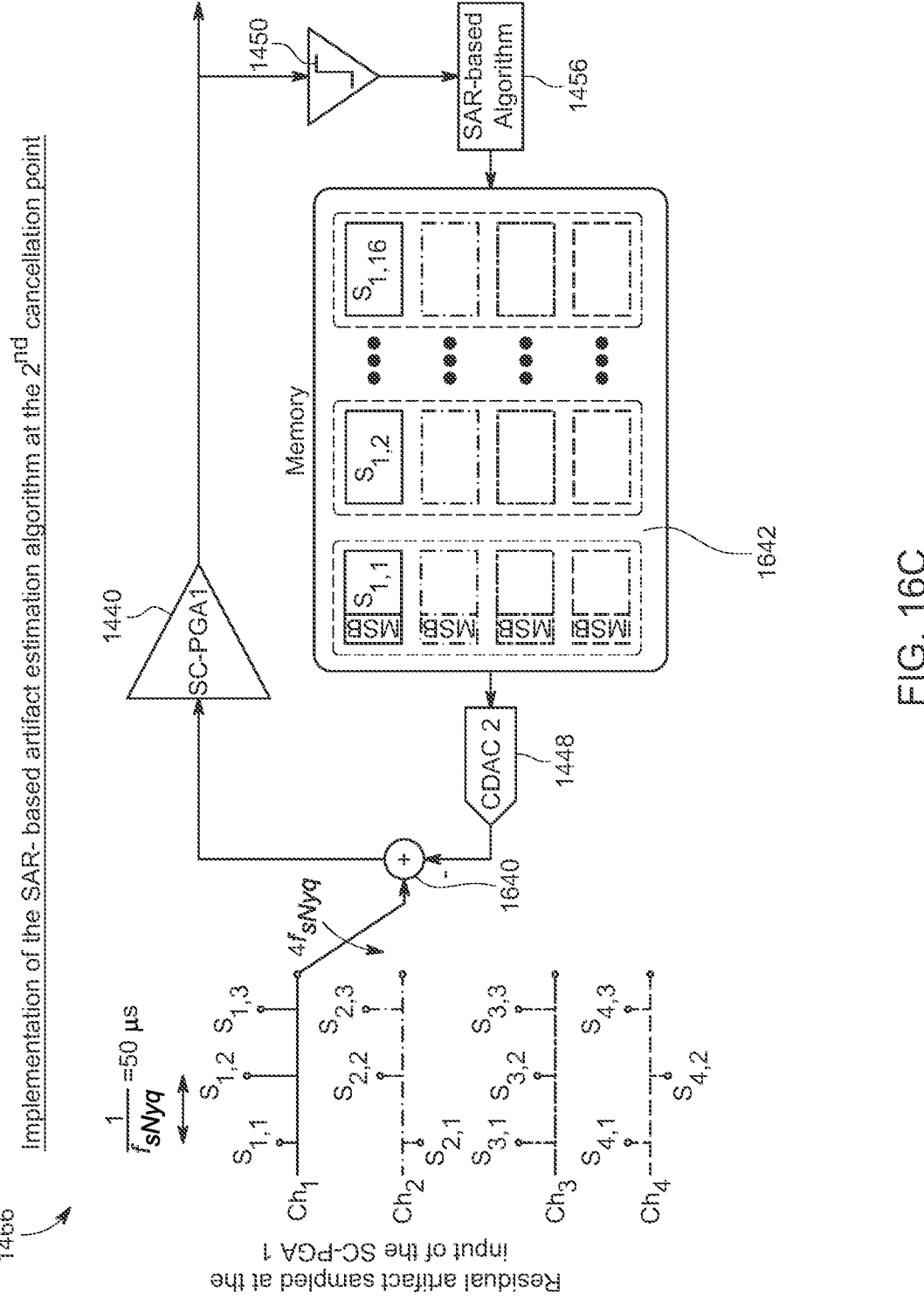
FIG. 16C shows an implementation of the second stage SAR-based cancellation to estimate the residual artifact present in each of the time-multiplexed channels in the example system in FIG. 14A, according to one or more embodiments of the present disclosure.

FIG. 16C shows a block diagram of the artifact estimation and cancellation at the second cancellation point (discrete-time domain) in FIG. 14A. Each of the four front end circuits 1410a-1410d constitute one of the four channels. The output of the front end circuits 1410a-1410d are multiplexed via a multiplexer 1640 and fed into the SC-PGA 1440. The output of the SC-PGA 1440 in FIG. 14A is fed to the comparator 1450. The output of the comparator 1450 is fed into the SAR based algorithm logic 1456 to output data stored into a memory 1642. The memory block 1642 provides the estimation of the residual DM artifact in each channel to the CDAC 1448.

Figure 16D:
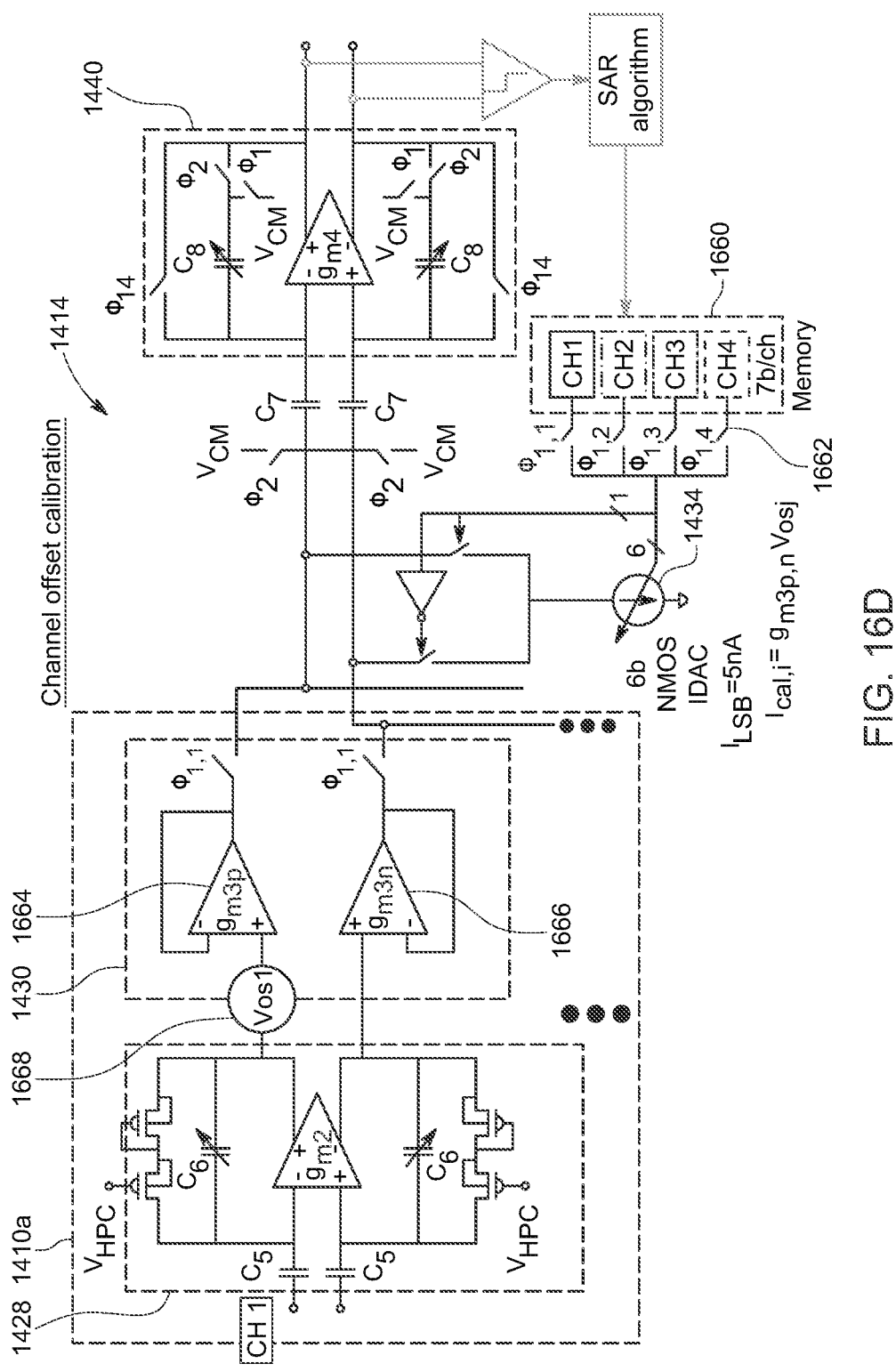
FIG. 16D illustrates a schematic of the channel offset calibration at the multiplexing node of the system in FIG. 14A, according to one or more embodiments of the present disclosure.

FIG. 16D shows a circuit diagram of the calibration circuit 1414 in FIG. 14A that is connected to the first channel front end circuit 1410a and the other front end circuits 1410b-1410c (not shown). The calibration circuit 1414 receives the output from the PGA 1440 and the buffer 1430 in the front end 1410a. The calibration circuit 1414 includes stored calibration values in a memory 1660. A bank of switches 1662 allows different calibration values corresponding to each front end channel circuit 1410a-1410d to be input into the DAC 1434 when the output of the channel is connected to the back end circuit 1412. Process variation during the chip fabrication can introduce mismatch in voltage buffers 1664 and 1666 that constitute the voltage buffer 1430. This creates a DC offset which can be modeled with a series DC voltage source as shown with a red circle block 1668 (Vos,1). Since the SC-PGA stages that follow the buffer 1430 amplify their input DC component, even a 1 mV offset at the buffer stage can introduce a 100's of mV offset at the ADC input. Therefore, the buffer offset has to be calibrated before propagating into the successive stages. By injecting a small current from the current source 1434 at the output of the buffer 1430, this offset can be mitigated. A SAR-based algorithm such as the SAR algorithm 1414 in FIG. 14A is implemented to automatically find the correct calibration current in successive approximation cycles.

FIG. 16E shows a waveform graph 1670 of the differential output of the SC-PGA 1442 prior to automatic offset calibration. A waveform graph 1672 shows the differential output of the SC-PGA 1442 after automatic offset calibration.

Figure 17:
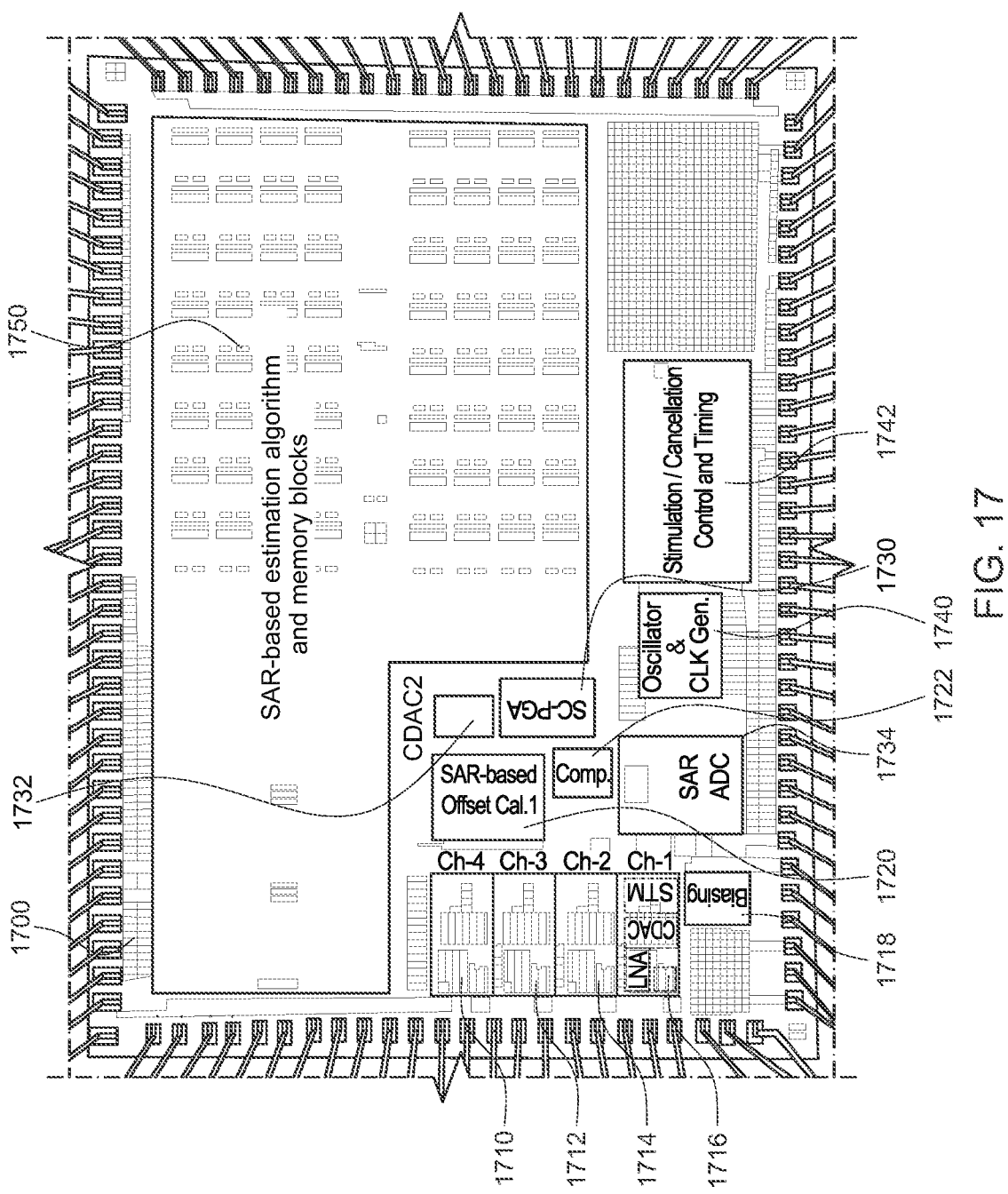
FIG. 17 illustrates an exemplary chip micrograph with the components of the system in FIG. 14A according to one or more embodiment of the present disclosure.

FIG. 17 shows a die layout 1700 of the example circuit 1400. The layout 1700 includes areas 1710, 1712, 1714, and 1716 that each include one of the front end stimulation and receiver channels 1410a-1410d in FIG. 14A. An area 1718 includes the reference current and bias generation circuitry. An area 1720 includes the offset circuitry 1414. An area 1722 includes the comparator 1450. An area 1730 includes the SC-PGAs 1440 and 1442. An area 1732 includes the CDAC 1448. An area 1734 includes the SAR based DAC 1444 in the backend circuit 1412. An area 1740 includes oscillator and clock generator circuitry. An area 1742 includes control and timing circuits. An area 1750 includes memory blocks and the SAR based estimation algorithm. The example circuit 1400 on the die layout 1700 improves the state-of-the-art artifact cancellation on-chip by more than 10×, while achieving 1200 mV$_{pp}$ DM and 700 mV$_{pp}$ CM artifact tolerance.

Figure 18A:
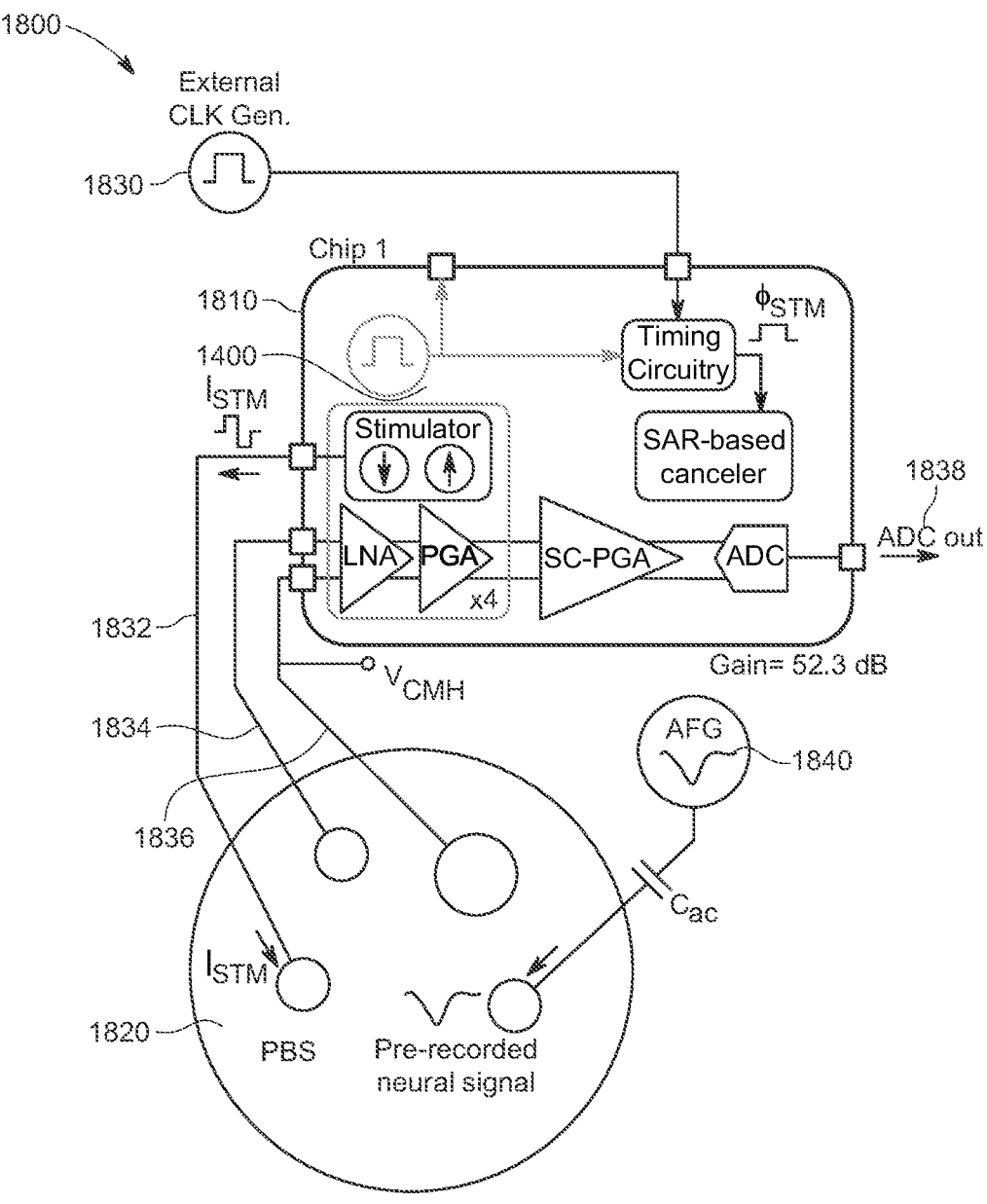
FIG. 18A illustrates a test set up for a system on chip with active cancellation for stimulation of an in vitro sample, according to one or more embodiments of the present disclosure.

FIG. 18A shows an example test system 1800 that demonstrates successful stimulation artifact cancellation based on the circuit 1400 in FIG. 14. The canceler operation of the test system 1800 is an in vitro setup to recover a neural signal contaminated with a stimulation artifact. The system 1800 includes a chip 1810 with the circuit 1400 that is connected to an in vitro test subject 1820. The chip 1810 is connected to an external clock generator 1830. The chip 1810 includes an output to a stimulation electrode 1832 for applying a stimulation signal to the test subject 1820. Two output electrodes 1834 and 1836 provide output signals from the stimulated test subject 1820. The chip 1810 includes an ADC output 1838. An artifact is simulated by the introduction of signal generated by an arbitrary function generator (AFG) 1840. A desired neural signal may be simulated by the introduction of signal generated by the AFG 1840.

Figure 18B:
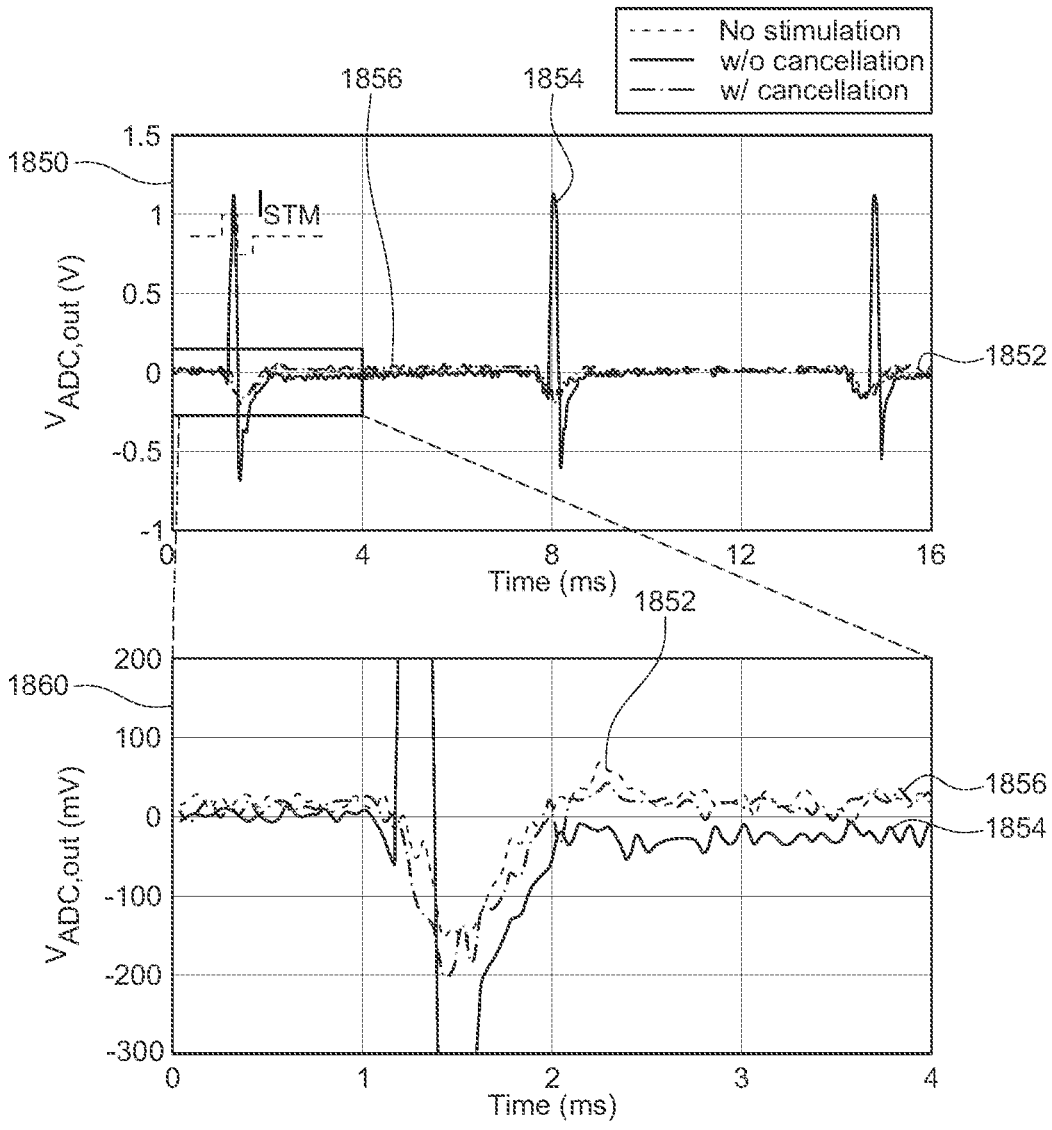
FIG. 18B illustrates graphs showing output signals of the performance of the canceler in vitro in FIG. 18A according to one or more embodiments of the present disclosure.

FIG. 18B shows a graph 1850 of the voltage output (V) 1838 of the ADC in the circuit 1400 with successful artifact cancellation leading to recovery of a neural signal in an in vitro experimental setup. The graph 1850 shows a trace 1852 of the output with no stimulation. A trace 1854 shows the output with no cancellation of the input signal. A trace 1856 shows the output signal after cancellation of the artifact in the input signal. Another inset graph 1860 shows a part of the graph 1850 where the traces 1852, 1854, and 1856 are shown on a smaller scale (mV).

Figure 19A:
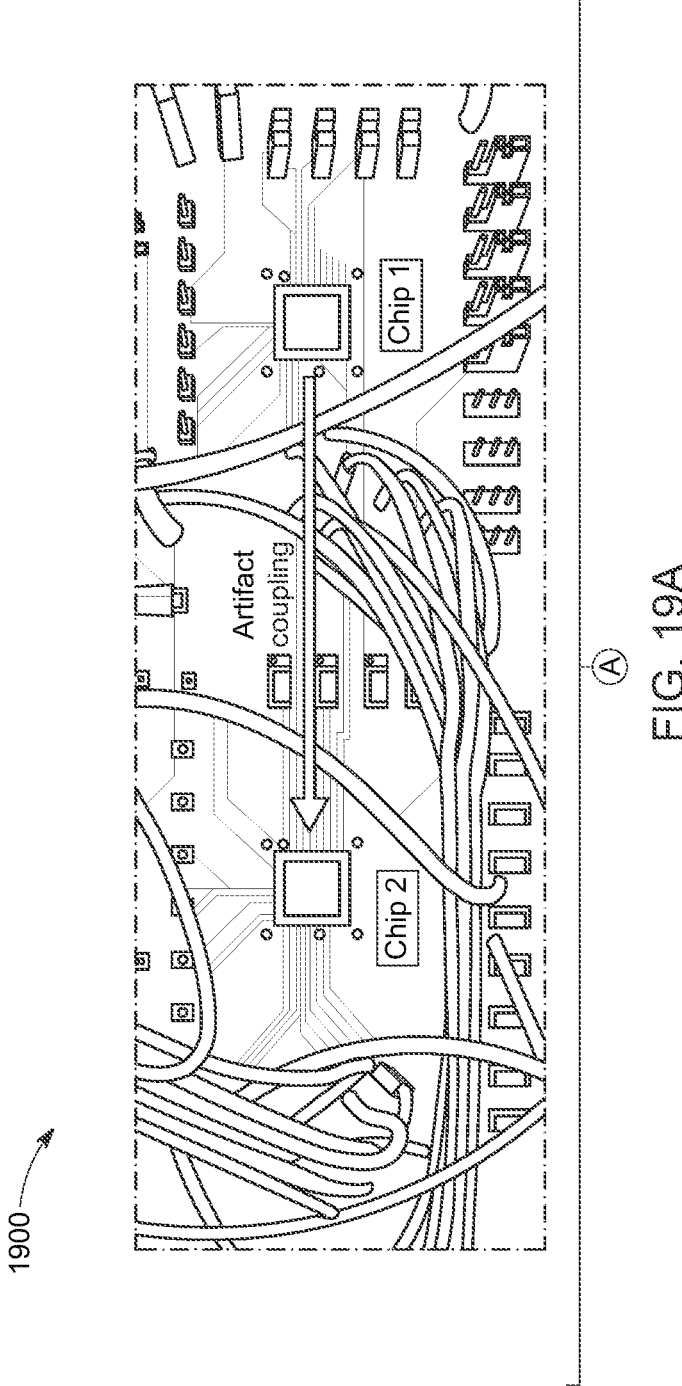
FIG. 19A is a diagram of a two chip canceler to estimate and cancel artifacts induced by other chips according to one or more embodiments of the present disclosure.

In a scaled-up example implementation, multiple chips may be used to interface with different regions of the brain to record the output from stimulation signals. In such scenario, the recording channels of a chip can pick up an artifact coupled from the stimulation of another chip. FIG. 19A shows an example scaled up implementation 1900 that uses two chips 1910 and 1920, both having cancellation circuits similar to the circuit 1400 in FIG. 14A. The system 1900 is where the stimulation artifact introduced by one integrated circuit (chip 1910) and is canceled by the second chip 1920. A clock input 1922 is coupled to both chips 1910 and 1920. In this example, the chip 1910 induces a stimulation signal applied by the on chip signal generator. An output 1924 of the chip 1910 injects the stimulation current to a resistive load, which mimics a biological tissue response. The output 1924 of the first chip 1910, which carries the stimulation artifact, is input into the second chip 1920 along with the output of an AFG 1926, which generates a single-tone desired signal. The components of the second chip 1920 are used solely for estimation and cancellation of the artifact generated from the first chip 1910, while amplifying the desired single-tone signal.

The above described cancellation scheme was tested in the 2-chip implementation 1900 shown in FIG. 19A. The stimulator on the first chip 1910 generates the artifact by applying a biphasic current to a resistive load and the cancellation circuits on the chip 1920 estimate and cancel the artifact coupled to their inputs.

Figure 19B:
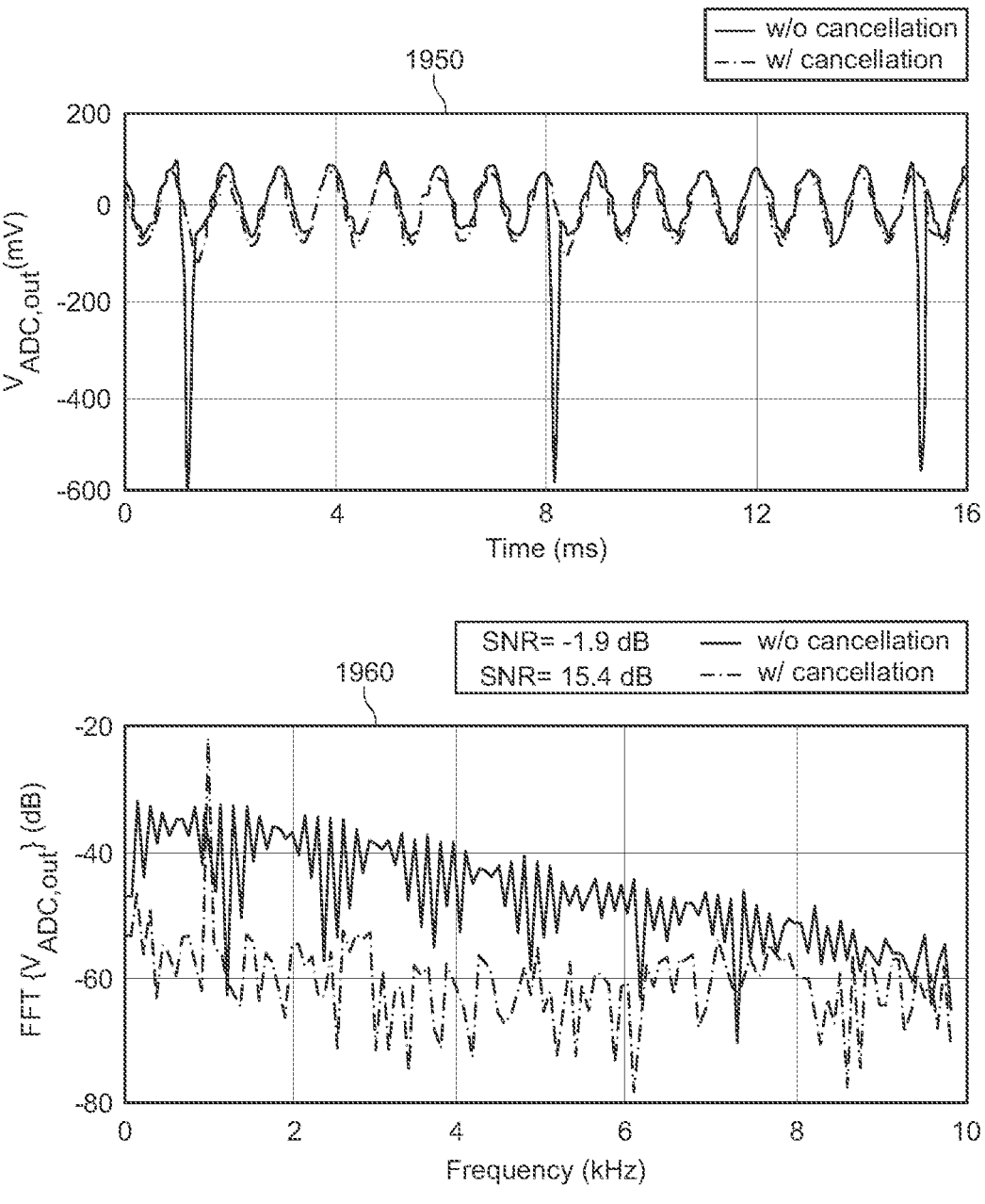
FIG. 19B is illustrates functionality of the canceler in FIG. 19A to estimate and cancel artifacts induced by other chips according to one or more embodiments of the present disclosure.

FIG. 19B shows a graph 1950 of the voltage output (V) of the ADC in the circuit 1920 with cancellation from the chip 1910 and without cancellation. Another graph 1960 shows the fast Fourier transfer (FFT) the voltage output (V) of the ADC in the circuit on the chip 1920 for the signal with cancellation and without cancellation.

FIG. 20 is a table 2000 compares the performance of the above described cancellation schemes in an example system on chip with state-of-the-art neural interfaces resilient to artifacts. The table 2000 includes columns that list known neural interfaces including ISSCC 21, JSSC 20, JSSC 18, ISSCC20, and JSSC 21 interfaces. FIG. 20 lists a set of parameters including the feature size, supply voltage, signal bandwidth, voltage gain, reference noise, ADC resolution, power per channel, area of the receiver, the number of receiver channels, maximum measurable input artifact and maximum artifact suppression for each of the neural interfaces in comparison with a chip that incorporates the cancellation circuits described above.

Figure 21:
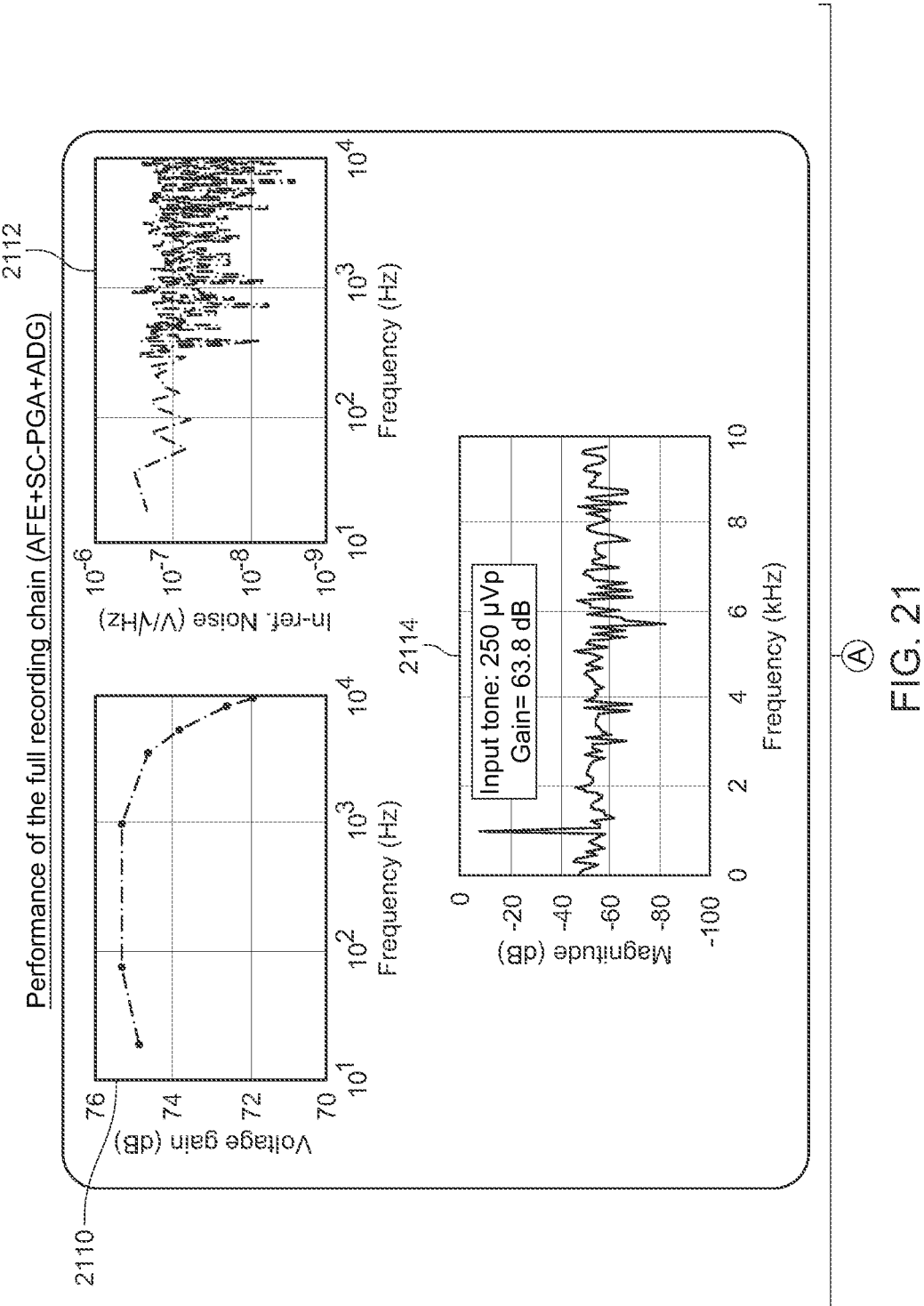
FIG. 21 is a series of graphs that illustrate the performance of the cancellation circuit according to one or more embodiments of the present disclosure.

FIG. 21 shows a series of graphs that illustrate AC performance of the recording chain in the example circuit 1400 from a single-tone test. A first graph 2110 shows voltage gain in decibels plotted against frequency. A second graph 2112 shows the input-referred noise spectral density of the full recording chain plotted against frequency. A third graph 2114 plots the magnitude of the signal in decibels plotted against frequency.

A second set of graphs show residual artifact at the ADC output in the presence of the CM and the DM artifact. Specifically, a graph 2120 shows traces with cancellation and without cancellation for 400 Vpp CM artifact cancellation. A graph 2122 shows traces with cancellation and without cancellation for 800 Vpp DM artifact cancellation. For both graphs 2120 and 2122, the receiver gain is 52.3 dB.

An image 2130 shows a differential signal output by the SC-PGA 1440 in FIG. 14A prior to input into the ADC measured without cancellation. An image 2132 shows a differential signal output by the SC-PGA 1440 in FIG. 14A prior to input into the ADC measured after artifact cancellation. The measured functionality of the canceler in the presence of a 400 $mV_{pp}$ artifact.

Computer and Hardware Implementation of the Disclosure

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. In one or more embodiments, computer-executable instructions are executed on a general purpose computer to turn the general purpose computer into a special purpose computer implementing elements of the disclosure. The computer executable instructions may be, for example, binaries, intermediate format instructions such as assembly language, or even source code. Although the subject matter has been described in language specific to structural marketing features and/or methodological acts, it is to be understood that the subject matter defined in the appended claims is not necessarily limited to the described marketing features or acts described above. Rather, the described marketing features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. In this description, "cloud computing" is defined as an un-subscription model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing un-subscription model can be composed of various characteristics such as, for example, on-demand self-service, broad network access, resource pooling, rapid elasticity, measured service, and so forth. A cloud-computing un-subscription model can also expose various service un-subscription models, such as, for example, Software as a Service ("SaaS"), a web service, Platform as a Service ("PaaS"), and Infrastructure as a Service ("IaaS"). A cloud-computing un-subscription model can also be deployed using different deployment un-subscription models such as private cloud, community cloud, public cloud, hybrid cloud, and so forth. In this description and in the claims, a "cloud-computing environment" is an environment in which cloud computing is employed.

In one example, a computing device may be configured to perform one or more of the processes described above. the computing device can comprise a processor, a memory, a storage device, an I/O interface, and a communication interface, which may be communicatively coupled by way of a communication infrastructure. In certain embodiments, the computing device can include fewer or more components than those described above.

In one or more embodiments, the processor includes hardware for executing instructions, such as those making up a computer program. As an example and not by way of limitation, to execute instructions for digitizing real-world objects, the processor may retrieve (or fetch) the instructions from an internal register, an internal cache, the memory, or the storage device and decode and execute them. The memory may be a volatile or non-volatile memory used for storing data, metadata, and programs for execution by the processor(s). The storage device includes storage, such as a hard disk, flash disk drive, or other digital storage device, for storing data or instructions related to object digitizing processes (e.g., digital scans, digital models).

The I/O interface allows a user to provide input to, receive output from, and otherwise transfer data to and receive data from computing device. The I/O interface may include a mouse, a keypad or a keyboard, a touch screen, a camera, an optical scanner, network interface, modem, other known I/O devices or a combination of such I/O interfaces. The I/O interface may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface is configured to provide graphical data to a display for presentation to a user. The graphical data may be representative of one or more graphical user interfaces and/or any other graphical content as may serve a particular implementation.

The communication interface can include hardware, software, or both. In any event, the communication interface can provide one or more interfaces for communication (such as, for example, packet-based communication) between the computing device and one or more other computing devices or networks. As an example and not by way of limitation, the communication interface may include a network interface controller (NIC) or network adapter for communicating with an Ethernet or other wire-based network or a wireless NIC (WNIC) or wireless adapter for communicating with a wireless network, such as a WI-FI.

Additionally, the communication interface may facilitate communications with various types of wired or wireless networks. The communication interface may also facilitate communications using various communication protocols. The communication infrastructure may also include hardware, software, or both that couples components of the computing device to each other. For example, the communication interface may use one or more networks and/or protocols to enable a plurality of computing devices connected by a particular infrastructure to communicate with each other to perform one or more aspects of the digitizing processes described herein. To illustrate, the image compression process can allow a plurality of devices (e.g., server devices for performing image processing tasks of a large number of images) to exchange information using various communication networks and protocols for exchanging information about a selected workflow and image data for a plurality of images.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "control system" on data stored on one or more computer-readable storage devices or received from other sources.

The term "control system" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

What is claimed is:

1. A signal recorder and stimulator system comprising:

a stimulation electrode operable to be attached to a sample;

a signal generator coupled to the stimulation electrode to provide a stimulation signal to the sample;

a detection electrode operable to be attached to the sample;

a signal recorder including:

an input coupled to the detection electrode, the input receiving an input signal from the sample stimulated by the stimulation signal applied by the stimulation electrode, the input signal including an artifact;

a first artifact estimation logic circuit coupled to the input producing a first artifact estimate;

a first subtraction logic circuit subtracting the first artifact estimation from the input signal to produce a first artifact cancelled signal;

a first low noise amplifier (LNA) receiving the first artifact cancelled signal and outputting an amplified first artifact cancelled signal;

a second artifact estimation logic circuit coupled to the input signal producing a second residual artifact estimate;

a second subtraction logic circuit coupled to the first subtraction logic circuit, the second subtraction logic circuit subtracting the estimate of the second residual artifact from the amplified first artifact cancelled signal to produce a second artifact cancelled signal; and an analog to digital converter (ADC) receiving the second artifact cancelled signal and outputting an output signal.

2. The signal recorder and stimulator system of claim 1, wherein the first and second estimation logic include a successive approximation register (SAR) scheme to estimate the estimation artifacts from the input signal.

3. The signal recorder and stimulator system of claim 1, wherein the first artifact estimation logic includes a common mode estimation logic for estimation of common mode of the artifact, and a differential mode estimation logic for estimation of differential mode of the artifact.

4. The signal recorder and stimulator system of claim 1, wherein the stimulation signal stimulates a selected neuron or neurons of the sample.

5. The signal recorder and stimulator system of claim 1, wherein the signal recorder is a system-on-chip (SoC).

6. The signal recorder and stimulator system of claim 1, further comprising:

an electrode coupled to the input;

a second low-noise amplifier (LNA) configured to receive the input signal from the electrode;

a gain amplifier configured to adjust a level of the electrical signals to a level appropriate for the ADC;

a filter configured to remove noise from the input signal; and a digital signal processor (DSP) coupled to the ADC.

7. The signal recorder and stimulator system of claim 6, wherein the DSP is further configured to estimate and subtract a third residual stimulation artifact from the output signal from the ADC.

8. The signal recorder and stimulator system of claim 7, wherein the first estimation of the artifact is subtracted from the input signal by the first subtraction logic at a first point before the LNA to cancel the artifact at a first point; and wherein the second estimate of the residual artifact is subtracted from the input signal by the second subtraction logic at a second point before the gain amplifier.

9. The signal recorder and stimulator system of claim 8, further comprising:

a first digital-to-analog converter (DAC) configured to convert a digital representation of the first artifact estimation into an analog waveform; and a second DAC configured to convert a digital representation of the second artifact estimation into an analog waveform.

10. The signal recorder and stimulator system of claim 6, further comprising:

a plurality of electrodes for receiving stimulation signals including the electrode;

a plurality of inputs including the input, each of the inputs coupled to one of the plurality of inputs;

multiple front end circuits, each having a stimulator and a low noise amplifier and defining a signal channel, wherein the low noise amplifier is part of one the multiple front end circuits, wherein each of the front end circuits are coupled to one of a plurality of inputs; and a multiplexer sending signals selected from the plurality of front end circuit to a back end circuit including the gain amplifier.

11. The signal recorder and stimulator system of claim 10 further comprising an offset circuit coupled to each of the channels.

12. The signal recorder and stimulator system of claim 1, wherein the artifact is one or more of electrical stimulation, magnetic stimulation, optical stimulation, or acoustic stimulation.

13. The signal recorder and stimulator system of claim 1, wherein a least-mean-square (LMS) algorithm trains the coefficients a finite-impulse-response (FIR) or infinite-impulse-response (IIR) filter to estimate the artifact.

14. The signal recorder and stimulator system of claim 1, further comprising a memory storing the first artifact estimation and the second artifact estimation, wherein the signal recorder includes an estimation phase to collect data from the input signal for determining the first and second artifact estimations.

15. A method of canceling an artifact on an input signal generated from a sample by a stimulation signal, the method comprising:

attaching a stimulation electrode to the sample;

providing the stimulation signal to the sample via a signal generator coupled to the stimulation electrode;

attaching a detection electrode to the sample;

receiving the input signal from the detection electrode from the sample;

determining a first estimation of the artifact via a first estimation logic circuit;

determining a second artifact estimation of a residual of the artifact on the input signal via a second estimation logic circuit;

subtracting the first artifact estimation from the input signal to produce a first artifact canceled signal that is input to a low noise amplifier; and subtracting the second artifact estimation from an output signal from the low noise amplifier to produce a second artifact canceled signal;

sending the second artifact canceled signal to a gain amplifier.

16. The method of claim 15, wherein the determination of the first and second artifact estimation is performed by a successive approximation register (SAR) scheme.

17. The method of claim 15, wherein the determination of the first artifact estimation includes estimating a common mode of the artifact, and estimating a differential mode of the artifact.

18. The method of claim 15, further comprising estimating and subtracting a third residual stimulation artifact from the input signal via a digital signal processor.

19. The method of claim 15, wherein the artifact is one or more of electrical stimulation, magnetic stimulation, optical stimulation, or acoustic stimulation.

20. The method of claim 15, further comprising:

storing the first artifact estimation and the second artifact estimation in a memory, wherein the determination of the first artifact estimation and second artifact estimation is determined in an estimation phase to collect data from the input signal; and wherein the subtraction of the first and second artifact estimations is performed in a cancelation phase; and repeating the estimation phase in response to a changed condition.

21. A responsive neurostimulation system comprising:

a stimulation electrode operable to be attached to a tissue;

a signal generator coupled to the electrode to provide a stimulation signal to the tissue;

a detection electrode operable to be attached to the tissue;

a signal recorder coupled to the detection electrode, the signal recorder including:

an input receiving an input signal from the detection electrode simultaneously with the signal generator providing the stimulation signal to the tissue;

a first artifact estimation logic circuit coupled to the input producing a first artifact estimate;

a first subtraction logic circuit subtracting the first artifact estimation from the input signal to produce a first artifact cancelled signal;

a first low noise amplifier (LNA) receiving the first artifact cancelled signal and outputting an amplified first artifact cancelled signal;

a second artifact estimation logic circuit coupled to the input signal producing a second residual artifact estimate;

a second subtraction logic circuit coupled to the first subtraction logic circuit, the second subtraction logic circuit subtracting the estimate of the second residual artifact from the amplified first artifact cancelled signal to produce a second artifact cancelled signal; and an analog to digital converter (ADC) receiving the second artifact cancelled signal and outputting an output signal.

\* \* \* \* \*